(12) United States Patent
Furuichi et al.

(10) Patent No.: US 11,179,059 B2
(45) Date of Patent: Nov. 23, 2021

(54) OPTICAL IMAGING APPARATUS FOR DIAGNOSIS AND IMAGE PROCESSING METHOD

(71) Applicant: TERUMO KABUSHIKI KAISHA, Tokyo (JP)

(72) Inventors: Junya Furuichi, Kanagawa (JP); Kenji Kaneko, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1183 days.

(21) Appl. No.: 15/431,969

(22) Filed: Feb. 14, 2017

(65) Prior Publication Data

US 2017/0150900 A1 Jun. 1, 2017

Related U.S. Application Data

(60) Division of application No. 14/036,468, filed on Sep. 25, 2013, now Pat. No. 9,615,771, which is a
(Continued)

(30) Foreign Application Priority Data

Mar. 25, 2011 (JP) .............................. JP2011-068628
Mar. 31, 2011 (JP) .............................. JP2011-078551

(51) Int. Cl.
*A61B 5/06* (2006.01)
*G06T 7/73* (2017.01)
(Continued)

(52) U.S. Cl.
CPC .......... *A61B 5/061* (2013.01); *A61B 1/00009* (2013.01); *A61B 5/0066* (2013.01);
(Continued)

(58) Field of Classification Search
CPC ..... A61B 5/06; A61B 5/02007; A61B 5/1077; A61B 5/0066; A61B 5/1079;
(Continued)

(56) References Cited

U.S. PATENT DOCUMENTS

2007/0167710 A1  7/2007  Unal et al.
2008/0075375 A1  3/2008  Unal
(Continued)

FOREIGN PATENT DOCUMENTS

JP  2010-014501 A  1/2010

OTHER PUBLICATIONS

International Search Report (PCT/ISA/210) dated Mar. 19, 2012, by the Japanese Patent Office as the International Searching Authority for International Application No. PCT/JP2012/001194.
(Continued)

*Primary Examiner* — Jonathan Cwern
(74) *Attorney, Agent, or Firm* — Buchanan Ingersoll & Rooney PC

(57) ABSTRACT

An optical imaging apparatus for diagnosis generates a closed curve which precisely reproduces the shape of the indwelled stent and the shape of the inner wall of the biological tissue at the indwelling position of the stent. The optical imaging apparatus analyzes intensity change in transmission direction of the light from the transmission and reception unit for every one of the respective line data; based on the result of the analysis detects pixel data expressing the stent position in the transmission direction; labels each pixel data expressing the detected stent position; eliminates, within the respective labeling groups applied with the same labels, labeling groups in each of which the number of pixel data in the circumferential direction is a predetermined value or less; calculates center position for each labeling group not
(Continued)

eliminated; and generates a stent closed-curve using the center position of each labeling group.

5 Claims, 18 Drawing Sheets

Related U.S. Application Data continuation of application No. PCT/JP2012/001194, filed on Feb. 22, 2012.

(51) Int. Cl.
    *A61B 5/00*     (2006.01)
    *A61B 5/02*     (2006.01)
    *A61B 5/107*     (2006.01)
    *A61B 1/00*     (2006.01)
    *G06T 7/70*     (2017.01)
    *G06T 7/00*     (2017.01)

(52) U.S. Cl.
    CPC .......... *A61B 5/0073* (2013.01); *A61B 5/0084* (2013.01); *A61B 5/02007* (2013.01); *A61B 5/06* (2013.01); *A61B 5/1076* (2013.01); *A61B 5/1077* (2013.01); *A61B 5/1079* (2013.01); *A61B 5/6852* (2013.01); *G06T 7/0012* (2013.01); *G06T 7/70* (2017.01); *G06T 7/73* (2017.01); *A61B 2576/02* (2013.01); *G06T 2207/10101* (2013.01); *G06T 2207/30101* (2013.01)

(58) Field of Classification Search
CPC ... A61B 5/1076; A61B 5/0084; A61B 5/0073; A61B 1/00009; A61B 5/6852; A61B 2576/02; G06T 7/0042; G06T 2207/30101; G06T 2207/10101
See application file for complete search history.

(56) References Cited

U.S. PATENT DOCUMENTS

| | | | |
|---|---|---|---|
| 2008/0317195 A1* | 12/2008 | Kobayashi | A61B 6/466 378/4 |
| 2010/0094127 A1 | 4/2010 | Xu | |
| 2011/0098966 A1 | 4/2011 | Suzuki | |
| 2012/0075638 A1 | 3/2012 | Rollins et al. | |

OTHER PUBLICATIONS

Kauffman C. et al.; "In Vivo Supervised Analysis of Stent Reendothelialization From Optical Coherence Tomography", IEE Transactions on Medical Imaging, IEEE Service Center, Piscataway, NJ., US, Mar. 1, 2010, vol. 29, No. 3 pp. 807-818.

Garret T. Bonnema et al.; "An Automatic Algorithm for Detecting Stent Endothelialization from Volumetric Optical Coherence Tomography Datasets; An Automatic Algorithm for Detecting Stent Endothelialization from Volumetric OCT Datasets", Physics in Medicine and Biology, Institute of Physics Publishing, Bristol, GB Jun. 21, 2008, vol. 53, No. 12, pp. 3083-3098.

Extended Search Report dated Jul. 16, 2014 by the European Patent Office, in corresponding European Patent Application No. 12765421.8 (15 pages).

* cited by examiner

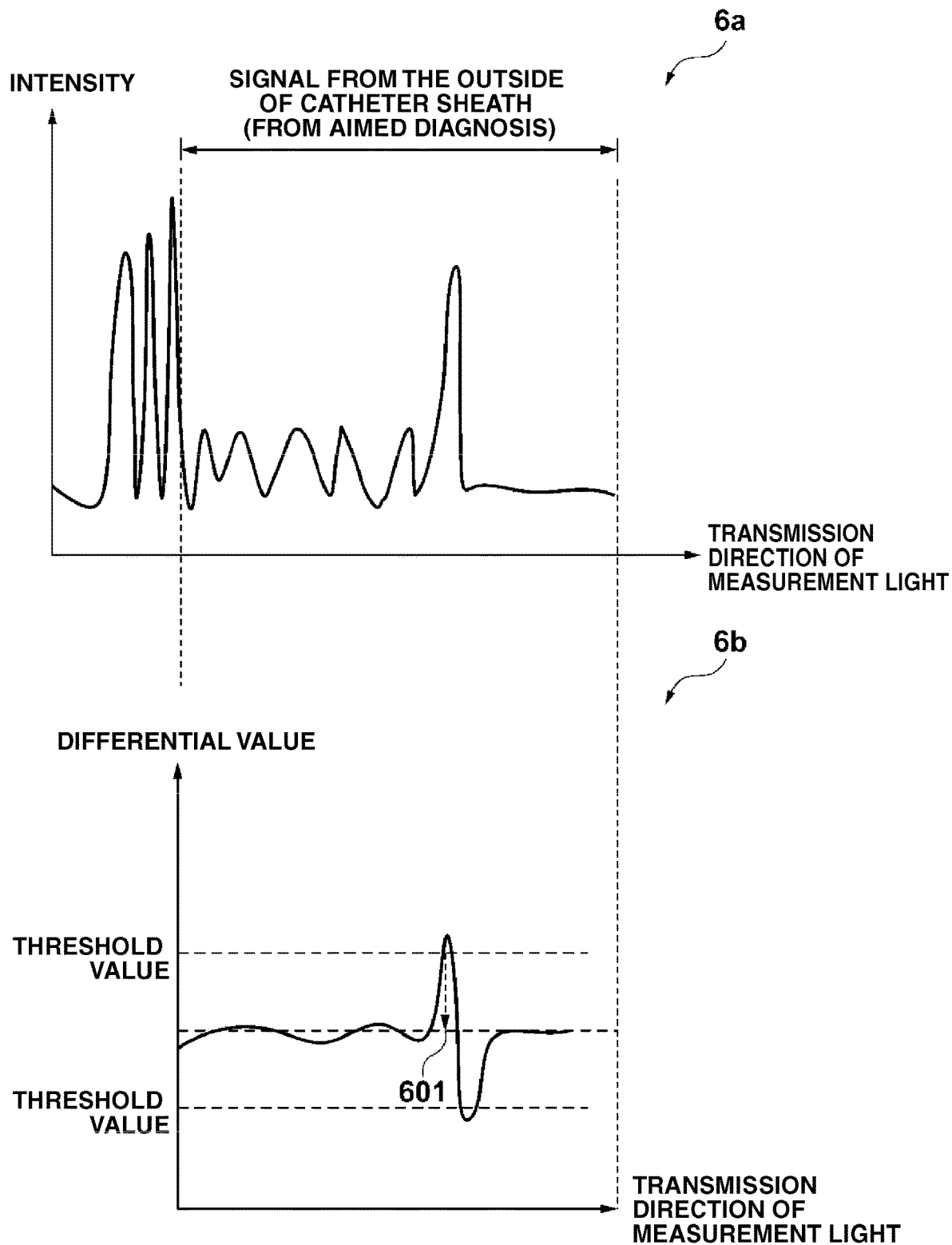

OPTICAL IMAGING APPARATUS FOR DIAGNOSIS AND IMAGE PROCESSING METHOD

CROSS REFERENCES TO RELATED APPLICATIONS

This application is a divisional application of U.S. application Ser. No. 14/036,468 filed on Sep. 25, 2013, which is a continuation application of International Application No. PCT/JP2012/001194 filed on Feb. 22, 2012, and claims priority to Japanese Application No. 2011-068628 filed on Mar. 25, 2011 and Japanese Application No. 2011-078551 filed on Mar. 31, 2011, the entire content of all four of which is incorporated herein by reference.

TECHNICAL FIELD

The present invention generally relates to an optical imaging apparatus for diagnosis and an image processing method.

BACKGROUND DISCUSSION

In the past, there have been used an optical coherent tomography (OCT) apparatus (see, for example, Japanese Application Publication No. 2010-14501) and an optical frequency domain imaging (OFDI) apparatus utilizing wavelength sweep, which is an improved type of optical coherent tomography apparatus, for a result confirmation after operation at the time of treatment inside a blood vessel depending on a high functional catheter such as a stent and the like. Hereinafter, in the present specification, the optical coherent tomography (OCT) apparatus and the optical frequency domain imaging (OFDI) apparatus utilizing wavelength sweep will be generically referred to as "optical imaging apparatus for diagnosis".

Specifically, these apparatus are utilized for specifying the position of a stent indwelled inside a body lumen (for example, inside a blood vessel) and the position of a biological tissue from an imaged tomographic image and for confirming an arrangement the stent takes with respect to the inner wall of the biological tissue.

Here, the stent is generally made of a metal through which the light cannot penetrate and is mesh-shaped. For this reason, the light illuminated from an optical probe is mostly reflected at the stent portion and does not reach the inner wall of the biological tissue, and so a situation arises in which only the light passing through aperture portions of the mesh will reach the inner wall. In consideration of such fact, in case of the tomographic image which is imaged by using an optical imaging apparatus for diagnosis, the stent and the inner wall will be respectively displayed as line segments which are discontinuous in the circumferential direction.

However, in a case in which the stent and the inner wall of the biological tissue are displayed as discontinuous line-segments, it becomes difficult for a user to comprehend the positional relationship between the stent and the inner wall, for example, to comprehend whether or not the stent is contacting the inner wall, whether or not the stent is spaced apart from the inner wall, or the like. Consequently, in an optical imaging apparatus for diagnosis, there is proposed a configuration in which a user can visually-comprehend the positional relationship between the stent and the inner wall, for example, by generating closed curves connecting the discontinuous line-segments (stent closed-curve and inner-wall closed-curve) and by displaying them by superimposing them on the tomographic image (for example, see U.S. Application Publication No. 2010/0094127.

However, in case of U.S. Application Publication No. 2010/0094127, there is not employed a construction in which noises in the region other than the stent and the inner wall are adequately removed, so that the generation of the closed curve will be carried out in a state in which noises of regions other than the stent and the inner wall are included. As a result, it can be assumed that the stent closed-curve and the inner-wall closed-curve, which are generated, will have shapes lacking in smoothness.

On the other hand, as mentioned above, because the stent is made of metal and has a certain amount of rigidity, there seldom happens a situation in which there occurs deformation accompanied by finely spaced concavity and convexity (precipitous concavity and convexity) in the circumferential direction with respect to the circular cross-sectional shape, and it is general that the stent becomes deformed to have a gradual curved-shape. In addition, also the inner wall of the biological tissue becomes deformed to have a gradual curved-shape in the circumferential direction with respect to the circular cross-sectional shape.

In consideration of such fact, it can be said, with regard to the closed curves of the stent and the inner wall of the biological tissue, that the fact of generating a more smooth shape precisely-reproduces the actual phenomenon inside the biological tissue (for example, blood vessel). Then, in order to reproduce such a closed curve, it becomes indispensable to exclude noises in the regions other than the stent and the inner wall as much as possible when generating the closed curve and to preliminarily-reduce the number of calculation points (number of stent candidate-points, number of inner-wall candidate-points) which are used for the generation of the closed curve.

However, when reducing the number of the calculation points too much, it is not possible to precisely-reproduce the cross-sectional shapes of the original stent and inner wall, and there is a possibility that there occurs a situation in which there are obtained shapes different from the cross-sectional shapes of the actual stent and inner wall. In consideration of such fact, it is desirable for the optical imaging apparatus for diagnosis to have a constitution in which the noises in the regions other than the stent and the inner wall are discriminated clearly from those of the stent and the inner wall, and in which the aforesaid noises can be removed reliably when generating the closed curves of the stent and the inner wall.

SUMMARY

The optical imaging apparatus for diagnosis disclosed here generates closed curves which relatively precisely-reproduce the shape of the indwelled stent and the shape of the inner wall of the biological tissue at the indwelling position of the aforesaid stent.

The optical imaging apparatus for diagnosis obtains reflection light from a biological tissue by moving a transmission and reception unit that carries out optical transmission and reception continuously toward axial direction while rotating the unit in circumferential direction in the inside of a body lumen, and which constructs a tomographic image of the biological tissue by using line data of interference light that is obtained by making the obtained reflection light and a reference light interfere with each other. The optical imaging apparatus includes a first analysis means for reading-out line data used for construction of a predetermined tomographic image and for analyzing intensity change in transmission direction of the light from the transmission and reception unit for every one of the respective line data, a first detection means, based on the analysis result by the first analysis means, for detecting pixel data expressing stent position in the transmission direction for every one of the respective line data, a first labeling means for labeling each pixel data expressing the stent position detected for every one of the respective line data based on each positional information, a first elimination means for eliminating, within the respective labeling groups applied with the same labels by the first labeling means, labeling groups in which the number of pixel data in circumferential direction, which is included in one labeling group, is a predetermined value or less, a first calculation means for calculating center position with regard to each labeling group, which was not eliminated by the first elimination means, based on positional information of each pixel data, and a first generation means for generating a stent closed-curve by using the center position of the each labeling group, which was calculated by the first calculation means.

According to the apparatus disclosed here, it becomes a situation in which it is possible, in the optical imaging apparatus for diagnosis, to generate closed curves which precisely-reproduce the shape of the indwelled stent and the shape of the inner wall of the biological tissue at the indwelling position of the aforesaid stent.

Other features and aspects of the optical imaging apparatus will become more apparent from the following explanation with reference to the accompanying drawings. In the accompanying drawings, the same reference numerals are applied to the same or similar constitutions.

BRIEF DESCRIPTION OF DRAWINGS

The attached drawings are included in the specification, constitute a portion of the disclosure, illustrate embodiments of the apparatus and method disclosed here by way of example, and are used for explaining principles of the apparatus and method disclosed here, together with the description.

FIG. 6A is a diagram explaining a general outline of a detection process of a stent candidate-point.

DETAILED DESCRIPTION

Figure 1:
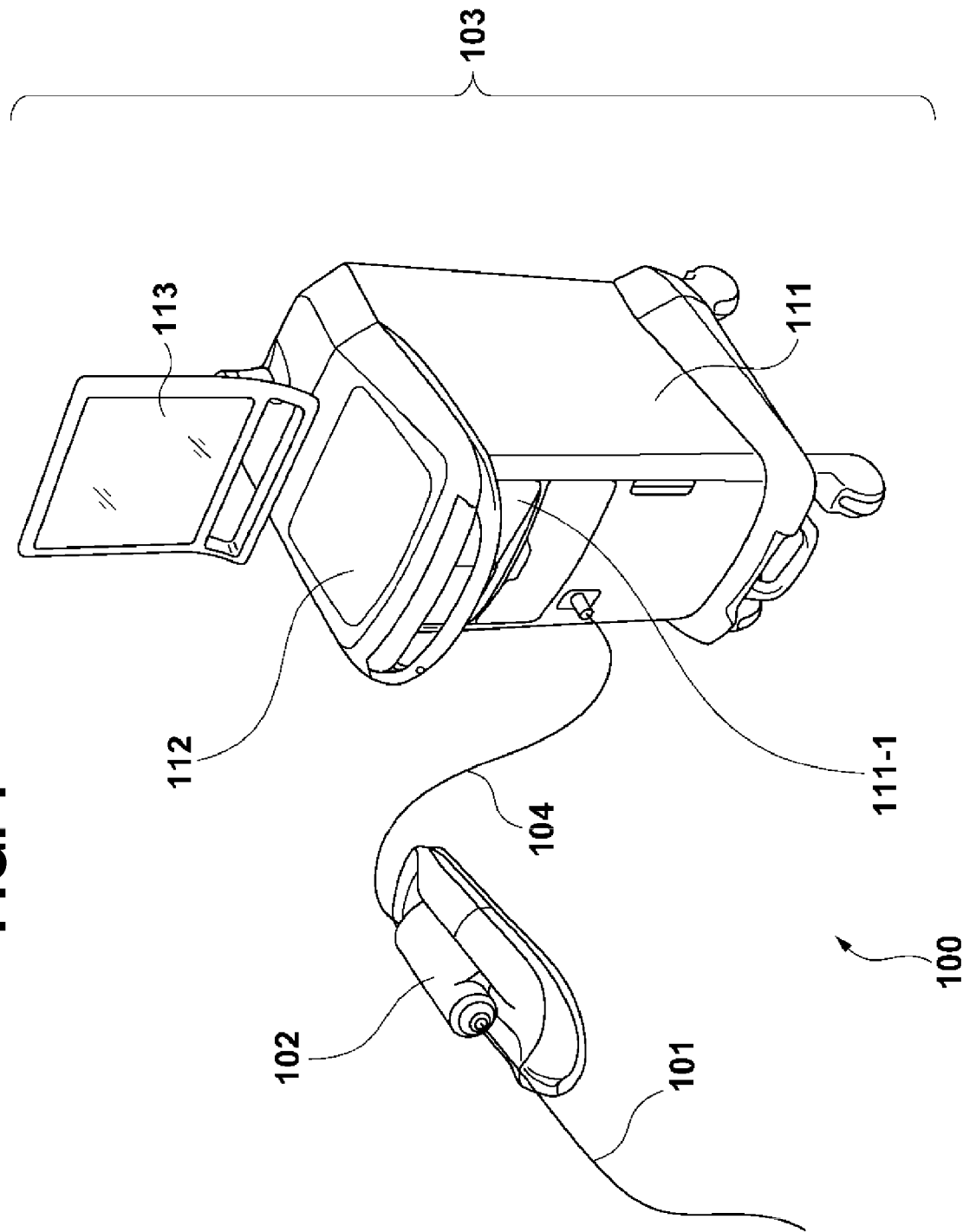
FIG. 1 is a perspective view of the outward-appearance of an optical imaging apparatus for diagnosis according to one embodiment disclosed here by way of example.

Hereinafter, respective embodiments of the apparatus and method representing examples of the apparatus and method disclosed here will be explained with reference to the attached drawings. The invention is not limited by the embodiments described below and shown in the drawing figures as various changes and alternations can be introduced and utilized.

First, there will be explained a general outline of an optical imaging apparatus for diagnosis relating to each embodiment disclosed here. For each embodiment of an optical imaging apparatus disclosed here, on an occasion of generating a stent closed-curve, stent candidate-points are extracted from respective line data constituting a tomographic image and thereafter, the extracted respective stent candidate-points are applied for labeling based on the positional information of the points. Then, a specific feature is included in an aspect wherein within the labeling groups for which the same labeling values are labeled, each labeling group in which the number of stent candidate-points in the circumferential direction, which is included in one labeling group, is a predetermined number or less will be excluded from the calculation target of the closed curve, representative points are extracted with regard to respective remaining labeling groups, and the closed curve is generated by using the aforesaid extracted representative points.

The fact that there is employed a constitution or configuration in which each labeling group, wherein the number of the stent candidate-points in the circumferential direction is a predetermined number or less, is excluded from the calculation target in this manner, is caused by the characteristics such as shown as follows which are specific in case of measuring the stent by using an optical imaging apparatus for diagnosis.

More specifically, the stent is made of metal, so that in the case of directing light to the stent, the intensity of the reflection light from the stent becomes very high compared with the intensity of the reflection light from the regions other than the stent. Therefore, for a tomographic image generated from the inside of the stent by a radial scan, the stent will be reproduced as a discontinuous line-segment having a circular shape without any defect. At that time, each line-segment is formed in the circumferential direction with a length equivalent to the thickness of the stent-mesh (for each line-segment, there never occurs a phenomenon in which a lack occurs for a portion thereof and fluctuation occurs for the length of the line-segment).

On the other hand, any noise from other portions than from the stent is displayed on an arbitrary position of the tomographic image, but there seldom happens a situation in which the noise is formed by a length equivalent to the thickness of the stent-mesh and at the same time, there are also few chances for the noise to be formed in the circumferential direction.

Therefore, on an occasion of discriminating the stent from a noise, it becomes possible to discriminate the stent clearly if assuming that a discrimination condition is set up according to the fact that there is displayed a line-segment having a length corresponding to the thickness of the mesh and also, according to the fact that the length of the line-segment is continuous along the circumferential direction.

In consideration of such fact, there is employed a constitution or configuration, in an optical imaging apparatus for diagnosis relating to each embodiment described below as examples of the imaging apparatus disclosed here, in which it is judged that a stent was hit (stent is present) in a case in which the number of stent candidate-points included in one labeling group is a predetermined number or more in the circumferential direction and it is judged that noise was hit (stent is not present) in a case in which the number of stent candidate-points is less than the predetermined number.

On the other hand, on an occasion of generating an inner-wall closed-curve of a biological tissue, a position, that is lowered as much as a certain amount from the position at which the intensity change of the reflection light becomes maximum in the transmission direction (referred to also as radial direction) of the measurement light for the respective line data constituting the tomographic image, is extracted as an inner-wall candidate-point, and each extracted inner-wall candidate-point is labeled based on the positional information of the point. Then, there is a feature that with regard to the labeling groups, within the labeling groups for which the same labeling values are labeled, in which the fluctuation, in the radial direction for the inner-wall candidate-points included in one labeling group, is a certain value or more, the labeling groups are excluded from the calculation target of the closed curve and with regard to the respective remaining labeling groups, representative points are extracted and the closed curve is generated by using such extracted representative points.

In this manner, there is employed a constitution or configuration in which there is extracted a position, which is lowered as much as a certain amount from the position at which the intensity change of the reflection light becomes maximum in the radial direction for the respective line data, as an inner-wall candidate-point and also there is employed a constitution or configuration in which with regard to the labeling groups in each of which the fluctuation in the radial direction for the inner-wall candidate-points has a certain value or more, the labeling groups are excluded from the calculation target, and this fact above is caused by the characteristics such as shown as follows which are specific in case of measuring the inner wall positioned at the outside of the stent by using an optical imaging apparatus for diagnosis.

More specifically, in a case in which the stent is indwelled in the inside of the biological tissue, the light reaching the inner wall is only the light which passed through the aperture portion of the stent-mesh. For this reason, while the inner wall is expressed and displayed by discontinuous line-segments on the tomographic image similar to the stent, there occurs fluctuation in the lengths of the line-segments (that is, such as the stent, it is not possible to carry out the discrimination thereof depending on the length of the line-segment in the circumferential direction).

On the other hand, the light which reaches the inner wall is not total-reflected by the inner wall and reaches a certain depth amount, so that a situation arises in which the intensity of the reflection light of the line data increases rapidly at the inner-wall position and maintains a high level as far as certain amount of depth (that is, it is possible to reliably-detect the position at which the reflection-light intensity of the line data becomes maximum and also, fluctuation of the positions in the radial direction in that case is also relatively little).

In consideration of such fact, in an optical imaging apparatus for diagnosis relating to each embodiment described below as examples of the imaging apparatus disclosed here, a position at which the reflection-light intensity of the line data is lowered from the maximum value by a certain amount is made an inner-wall candidate-point. Then, there is employed a constitution or configuration in which it is judged that an inner wall was hit in a case in which the fluctuation, in the radial direction for the inner-wall candidate-points included in one labeling group, is a predetermined value or less and it is judged that a noise was hit in a case in which the fluctuation is larger than the predetermined value.

Set forth next is a description of respective embodiments of the optical imaging apparatus and method disclosed here.

First Embodiment

1. Outward-Appearance Constitution of Optical Imaging Apparatus for Diagnosis

FIG. 1 is a perspective view of an optical imaging diagnostic apparatus (optical coherent tomography apparatus or optical frequency domain imaging apparatus utilizing wavelength sweep) 100 according to an embodiment representing one example of the optical imaging apparatus and method disclosed here.

As shown in FIG. 1, the optical imaging diagnostic apparatus 100 is provided with an optical probe unit 101, a scanner & pull-back unit 102 and an operation control apparatus 103, and the scanner & pull-back unit 102 and the operation control apparatus 103 are connected by a signal line 104.

The optical probe unit 101 is inserted directly inside a body lumen of a blood vessel or the like and transmits the transmitted measurement light continuously toward the biological tissue and concurrently, is inserted with an imaging core which is provided, at the distal end of the imaging core, with a transmission and receiving unit for receiving the reflected light from the biological tissue continuously, and a state of the biological tissue is measured by using the imaging core.

The scanner & pull-back unit 102 is constituted or configured such that the optical probe unit 101 is attached to the scanner & pull-back unit 102 in a detachable manner and realizes or undergoes a radial scan (operation in the axial direction and operation in the rotation direction inside the body lumen) of the imaging core inserted in the optical probe unit 101 by the driving operation of the an installed motor. Also, a reflected light received by the transmitting and receiving unit is obtained and concurrently, the obtained reflected light is transmitted to the operation control apparatus 103 through the signal line 104.

The operation control apparatus 103 is configured to permit input of various kinds of set values on an occasion of measurement and to display the measurement result as tomographic images of the biological tissue.

In the operation control apparatus 103, the reference numeral 111 indicates a main body control unit. Coherent light data are generated by causing the reflected light obtained by the measurement and the reference light obtained by separating the measurement light interfere with each other and concurrently, multiple tomographic images are constructed in the axial direction inside the body lumen by processing the line data generated based on the coherent light data.

The operation control apparatus 103 also includes a printer & DVD recorder 111-1, so that the processed result in the main body control unit 111 can be printed while also being stored as data signals. The operation control apparatus 103 additionally includes an operation panel 112, allowing a user to input various kinds of set values and instructions through the operation panel 112, and an LCD monitor 113 serving as a display apparatus which displays a plurality of tomographic images of the biological tissue, which are constructed in the main body control unit 111.

2. Functional Constitution of Optical Imaging Apparatus for Diagnosis

Next, there will be explained a functional constitution or configuration of the optical imaging apparatus for diagnosis 100. As mentioned above, the optical imaging apparatus for diagnosis can be an optical coherent tomography apparatus (OCT) and an optical frequency domain imaging (OFDI) apparatus utilizing wavelength sweep. The description which follows explains, by way of example, an optical frequency domain imaging (OFDI) apparatus utilizing wavelength sweep.

Figure 2:
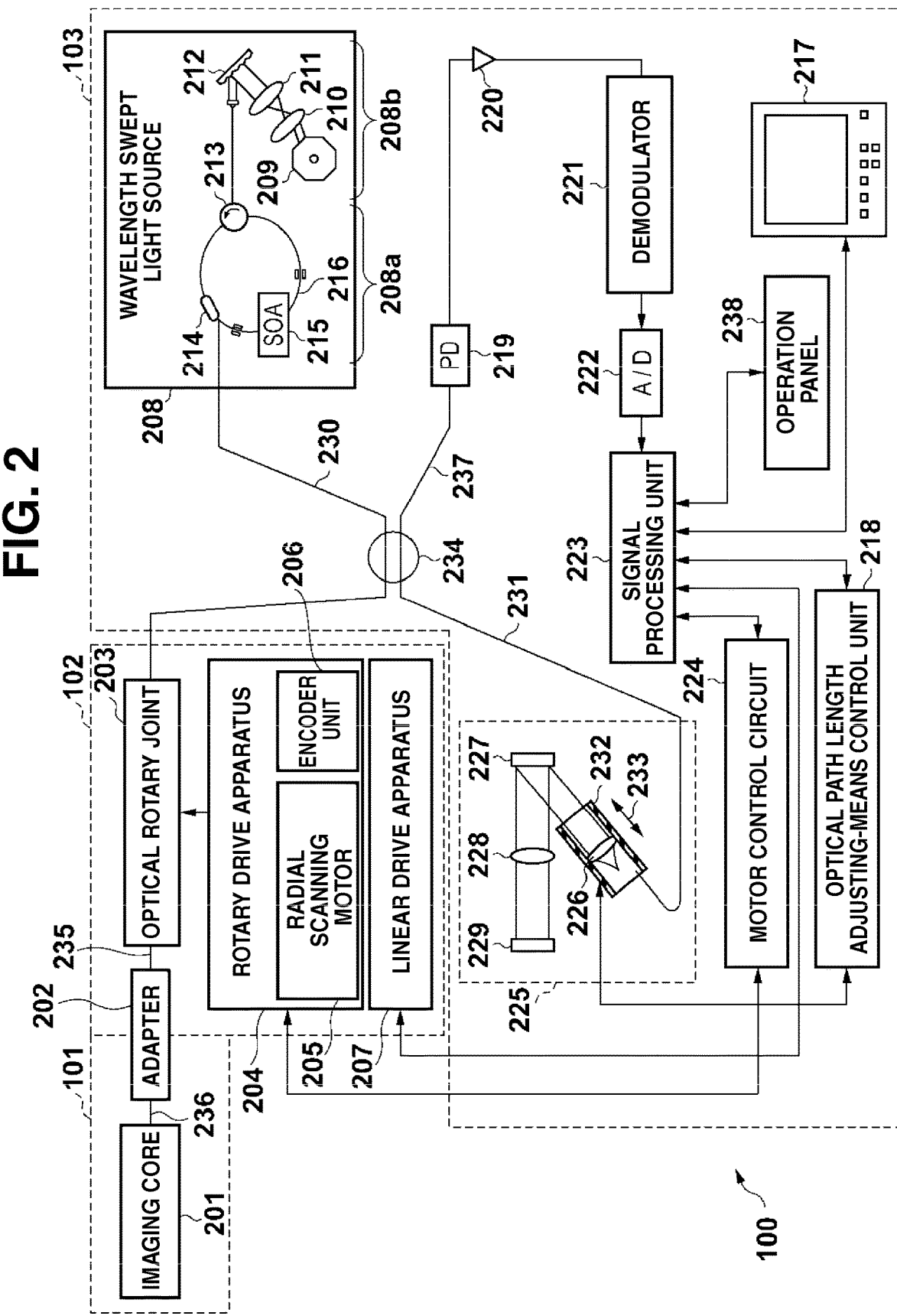
FIG. 2 is a diagram showing a functional constitution of an optical imaging apparatus for diagnosis.

FIG. 2 shows a functional constitution or configuration of the optical coherent tomography apparatus utilizing wavelength sweep representing one example of an optical imaging apparatus for diagnosis 100. The reference numeral 208 indicates a wavelength-swept light source and a Swept Laser is used. The wavelength-swept light source 208 using the Swept Laser is one kind of an Extended-cavity Laser which is composed of an optical fiber 216 connected with a SOA (semiconductor optical amplifier) 215 having a ring shape and a polygon scanning filter (208b).

The light outputted from the SOA 215 proceeds inside the optical fiber 216 and enters in the polygon scanning filter 208b and the wavelength selected here is amplified by the SOA 215 and finally, it is outputted from a coupler 214.

In the polygon scanning filter 208b, the wavelength is selected depending on the combination of a diffraction lattice 212 for light-splitting the light and a polygon mirror 209. Specifically, the light which is light-split by the diffraction lattice 212 is focused on the surface of the polygon mirror 209 depending on two pieces of lenses (210, 211). Thus, it happens that only the light of the wavelength perpendicular to the polygon mirror 209 returns to the same optical path and is outputted from the polygon scanning filter 208b. Consequently, it is possible to carry out the time sweep of the wavelength by rotating the polygon mirror 209.

For the polygon mirror 209, for example, a dotriacontahedron mirror is used and the rotation speed thereof is around 50000 rpm. Owing to the wavelength sweep system in which the polygon mirror 209 and the diffraction lattice 212 are combined, it is possible to employ a high speed and high power wavelength sweep.

The light of the wavelength swept light source 208, which is outputted from a coupler 214, enters one end of a first single mode fiber 230 and is transmitted to the distal end side. The first single mode fiber 230 is optically connected with a second single mode fiber 237 and a third single mode fiber 231 in a photo coupler unit 234 positioned along the length of the first single mode fiber 230. Therefore, light entering the first single mode fiber 230 is transmitted by being split into three optical paths at the maximum by this photo coupler unit 234.

On the distal end side ahead the photo coupler unit 234 of the first single mode fiber 230, there is provided, in the scanner & pullback unit 102, an optical rotary joint (optical coupling portion) 203 which connects between a non-rotary portion (fixed portion) and a rotary portion (rotational drive unit) and which transmits the light.

Further, on the distal end side of a fourth single mode fiber 235 in the inside of the optical rotary joint (optical coupling portion) 203, there is connected a fifth single mode fiber 236 of the optical probe unit 101 in a freely detachable manner through an adapter 202. Consequently, the light from the wavelength swept light source 208 is transmitted to the fifth single mode fiber 236 which is passed-through the imaging core 201 and which is rotary-drivable.

The transmitted light is illuminated from a distal end side of the imaging core 201 with respect to the biological tissue while being radially operated (rotated). Then, a portion of the reflected light which is scattered on the surface of or in the inside of the biological tissue is taken-in by the imaging core 201 and returns to the first single mode fiber 230 side through the reverse optical path. Further, the light is light-received by a photo detector (for example, photo diode 219) after a portion of the light moves to the second single mode fiber 237 side by the photo coupler unit 234 and is emitted from one end of the second single mode fiber 237.

The rotational drive unit side of the optical rotary joint 203 is rotationally driven by a radial scanning motor 205 of the rotary drive apparatus 204. Also, the rotary angle of the radial scanning motor 205 is detected by an encoder unit 206. Further, the scanner & pull-back unit 102 is provided with a linear drive apparatus 207 which produces the axial-direction operation of the imaging core 201 based on an instruction from a signal processing unit 223.

On the other hand, there is provided a variable mechanism 225 of the optical path length for fine-adjusting the optical path length of the reference light at a distal end on the opposite side with respect to the photo coupler unit 234 of the third single mode fiber 231.

This variable mechanism 225 of the optical path length is provided with an optical path length changing means for changing the optical path length which corresponds to the fluctuation of the length of the optical path such that the fluctuation of the length of the individual optical probe unit 101 can be absorbed in the case of the optical probe unit 101 being exchanged with a another optical probe unit 101.

The third single mode fiber 231 and a collimating lens 226 are provided on a one-axis stage 232 which is freely movable in the optical axis direction of the one-axis stage 232 as shown by an arrow 233, and they form an optical path length changing means.

Specifically, in case of exchanging the optical probe unit 101, the one-axis stage 232 functions as the optical path length changing means having such an amount of variable range of the optical path length, which can absorb the fluctuation of the optical path length of the optical probe unit 101. Further, the one-axis stage 232 is provided also with a function as an adjusting means for adjusting an offset. For example, even in a case in which the distal end of the optical probe unit 101 is not closely-attached to the surface of the biological tissue, it is possible, by minutely changing the optical path length by the one-axis stage, to set it to a state of interference with the reflected light from the surface position of the biological tissue.

The light whose optical path length is fine-adjusted by the variable mechanism 225 of the optical path length is mixed with the light obtained from the first single mode fiber 230 side by the photo coupler unit 234 which is provided along the third single mode fiber 231 and is light-received by the photo diode 219.

The coherent light which is light-received by the photo diode 219 in this manner is photoelectrically converted and amplified by an amplifier 220 and, thereafter, is inputted to a demodulator 221. In this demodulator 221, a demodulation process for extracting only the signal component of the coherent light is carried out and the output of the demodulator 221 is inputted to an A/D converter 222 as the coherent light signal.

In the A/D converter 222, the coherent light signal is subjected to sampling, for example, at 180 MHz for 2048 points and digital data (coherent light data) of one line are generated. The reason the sampling frequency is set at 180 MHz is due to an assumption that about 90% of the period of wavelength sweep (12.5 μsec) is to be extracted as digital data of 2048 points in case of setting the repetition frequency of wavelength sweep at 40 kHz and it is not limited by this aspect in particular.

The coherent light data of one line unit, generated in the A/D converter 222, are inputted to the signal processing unit 223. In case of a measurement mode, in the signal processing unit 223, the coherent light data are frequency-decomposed by FFT (Fast Fourier Transform) and then, there are generated data in the depth direction (line data), and by coordinate-converting those data, there is constructed a tomographic image at each position inside the biological tissue and it is outputted to an LCD monitor 217 (corresponding to reference numeral 113 of FIG. 1) at a predetermined frame rate.

The signal processing unit 223 is connected further with an optical path length adjusting-means control apparatus 218. The signal processing unit 223 carries out control of the position of the one-axis stage 232 by the optical path length adjusting-means control apparatus 218. Also, the signal processing unit 223 is connected with a motor control circuit 224 and receives a video synchronization signal of the motor control circuit 224. In the signal processing unit 223, the construction of the tomographic image is carried out in synchronization with the received video synchronization signal.

In addition, the video synchronization signal of this motor control circuit 224 is transmitted also to the rotary drive apparatus 204 and the rotary drive apparatus 204 outputs a drive signal which is in synchronization with the video synchronization signal.

3. Functional Constitution of Signal Processing Unit

Figure 3:
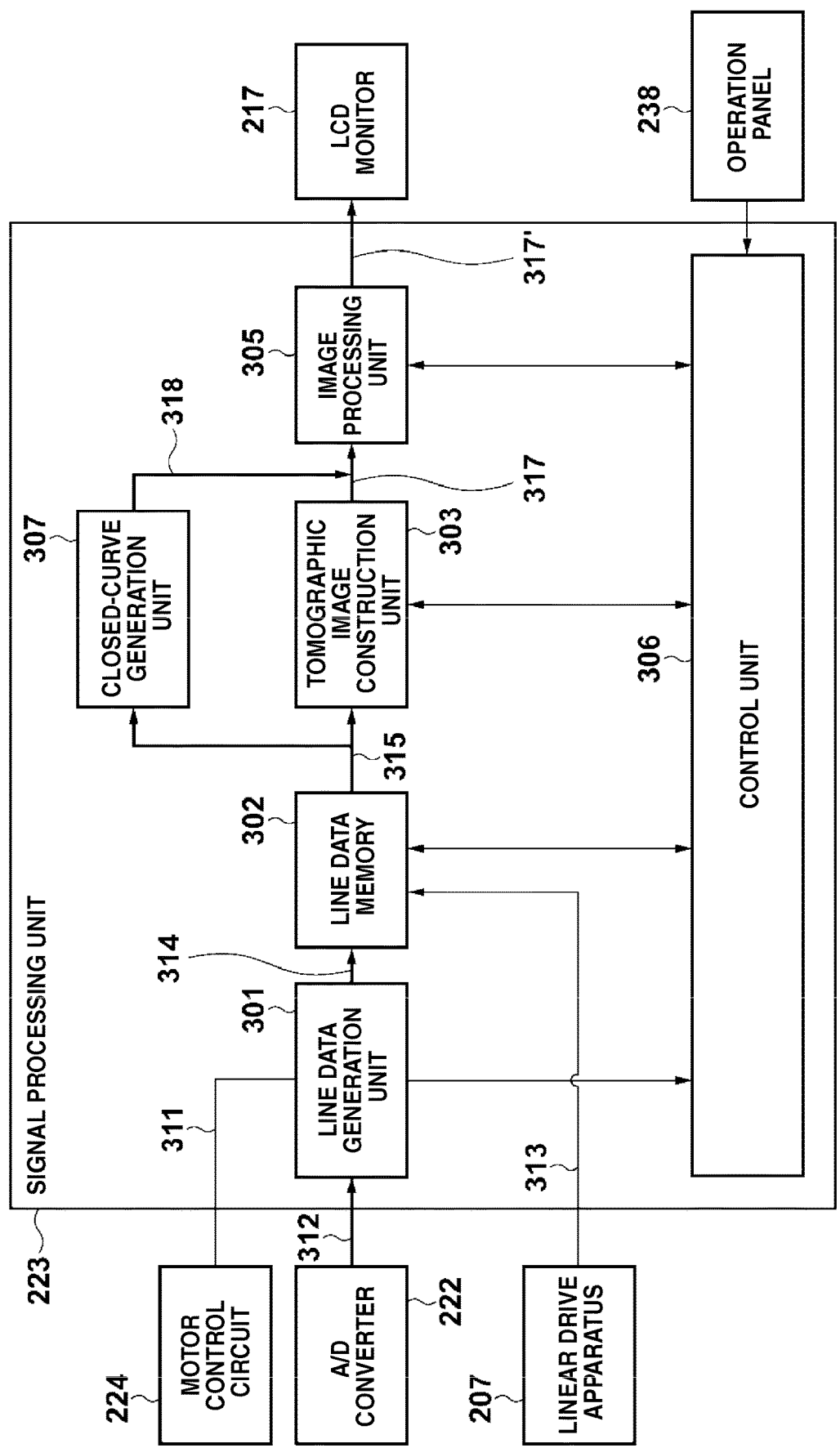
FIG. 3 is a diagram showing a functional constitution of a signal processing unit.

Set forth next with reference to FIG. 3 is a description of the functional constitution or configuration of the signal processing unit 223 for realizing a construction process of the tomographic image and a closed-curve generation process based on the line data utilized for the construction of the tomographic image in the signal processing unit 223 of the imaging apparatus for diagnosis 100. It is possible for the construction process and the generation process, which will be explained hereinafter, to be realized using dedicated hardware and also to be realized by software (by a configuration in which a computer executes programs).

FIG. 3 is a diagram showing a functional constitution or configuration and a functional block associated therewith for realizing the construction process and the generation process in the signal processing unit 223 of the optical imaging apparatus for diagnosis 100.

As shown in FIG. 3, the coherent light data generated in the A/D converter 222 is processed in a line data generation unit 301 inside the signal processing portion 223 such that the number of lines per rotation of the radial scanning motor is 512 by using a signal of the encoder unit 206 of the radial scanning motor 205, which is outputted from the motor control circuit 224.

It is assumed here, as one example, that the tomographic image is to be composed of 512 lines, but the number of lines is not limited by this number.

The line data 314 outputted from the line data generation unit 301 is stored in the line data memory 302 for every one rotation of the radial scanning motor based on an instruction from the control unit 306. At that time, in the control unit 306, a pulse signal 313 outputted from a moving amount detector of the linear drive apparatus 207 is counted beforehand and thereafter, when storing the line data 314 into the line data memory 30, the storing is carried out by being correlated with the count values when the respective line data 314 were generated.

The foregoing description explains that the line data memory 302 is arranged and the line data 314 is stored by correlating the line data with the count value of the pulse signal 313 outputted from the moving amount detector of the linear drive apparatus 207, but the present invention is not limited by this aspect. For example, a constitution or configuration is possible in which a tomographic image data memory is arranged behind the tomographic image construction unit 303 and the tomographic image 317 is stored in such a manner as to be correlated with the count value of the pulse signal 313 outputted from the moving amount detector of the linear drive apparatus 207.

Referring once again to FIG. 3, based on the instruction from the control unit 306, the line data 315 stored by being correlated with the count value is subjected to various kinds of processes (line addition-averaging process, filtering process and the like) in the tomographic image construction unit 303 and thereafter, is sequentially outputted as tomographic images 317 by being Rθ-converted.

Further, in the image processing unit 305, image processing for displaying on the LCD monitor 217 is applied and thereafter, it is outputted to the LCD monitor 217 as a lateral tomographic image 317'.

Also, the line data 315 stored by being correlated with the count value is read into the closed-curve generation unit 307 based on the instruction from the control unit 306, and there is executed a process of generating a closed curve expressing the stent position and a closed curve expressing the inner-wall position. The generated closed-curve (stent closed-curve, inner-wall closed-curve) data 318 are inputted into the image processing unit 305 and superimposed with the tomographic image 317'. Details of the closed-curve generation process in the closed-curve generation unit 307 will be described later.

In the LCD monitor 217, the tomographic image 317' processed in the image processing unit 305 is displayed. Also, in a case in which a closed-curve generation instruction is inputted by a user through the operation panel 238, there is displayed a tomographic image 317' superimposed with the closed-curve which is generated in the closed-curve generation unit 307. The operation panel 238 is an example of an input means for inputting information identifying a thickness of the stent.

4. Constitution of Tomographic Image Data

Figure 4:
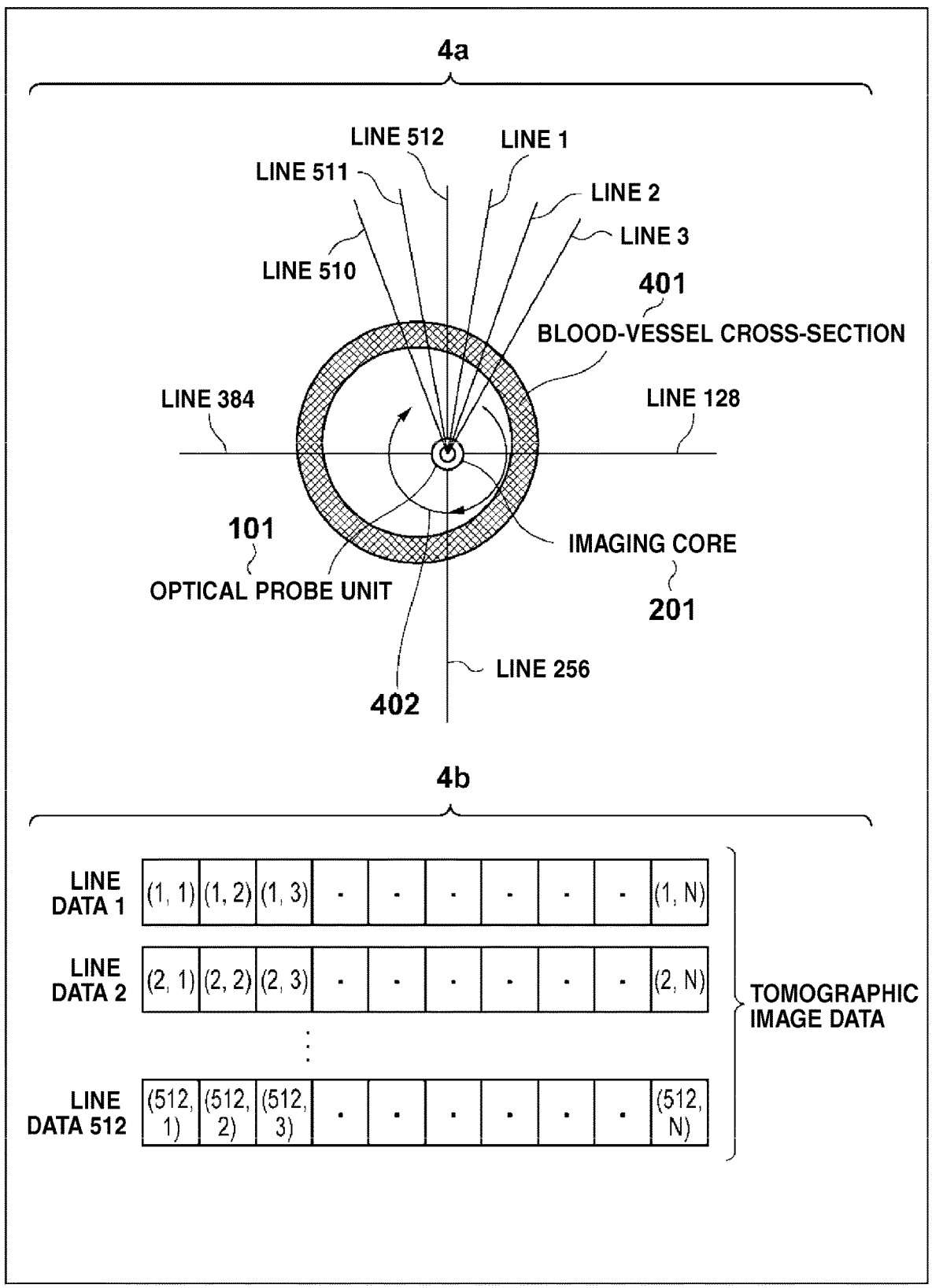
FIG. 4 is a diagram showing a data structure of a generated tomographic image.

Set forth next with reference to FIG. 4 is an explanation of the constitution or configuration of tomographic image data constructed by the tomographic image construction unit 303. FIG. 4 illustrates a relationship between a radial operation in the imaging core of the optical probe unit 101 and the line data constituting the tomographic image data.

In 4a of FIG. 4, a reference numeral 401 indicates a cross-section of a biological tissue into which the optical probe unit 101 is inserted. As discussed above, there is attached a transmission and reception unit at the distal portion of the imaging core 201 which is inserted into the optical probe unit 101 and this is rotated toward an arrow 402 direction by the radial scanning motor 205.

The transmitting & receiving of the measurement light is carried out by each rotary angle depending on the transmission and reception unit. Lines 1, 2, . . . , 512 show the transmitting direction of measurement light at each rotary angle. In this embodiment of the optical imaging apparatus for diagnosis 100, the transmitting & receiving of the measurement light are carried out intermittently 512 times during the time when the transmission and reception unit rotates 360 degrees at a predetermined cross-section (predetermined axial position) of a biological tissue 401. The number of times of transmitting & receiving of the measurement light during each 360 degree rotation is not limited to 512 and it is can be optionally settable.

The portion of FIG. 4 identified as 4b shows a constitution or configuration of line data which are obtained by transmitting & receiving the measurement light at respective rotary angles. As shown in 4b of FIG. 4, the tomographic image data in this exemplified embodiment are constituted by a line data group of 512 lines and each of the line data is constituted by N-number of pixel data group in the transmission direction of the measurement light (N is, for example, 1024).

The transmission & reception of such a measurement light is carried out while progressing toward the axial direction inside the body lumen, so that the line data group shown in 4b of FIG. 4 is generated by a plurality of sets along the axial direction. Note that the scan (scanning) which repeats the transmission & reception of the signal by the transmission and reception unit at each of the cross-sections of the biological tissue in conformity with the progress of the imaging core 201 toward the axial direction is referred to generally as "radial scan (radial scanning)".

5. Flow of Closed-Curve Generation Process

Figure 5:
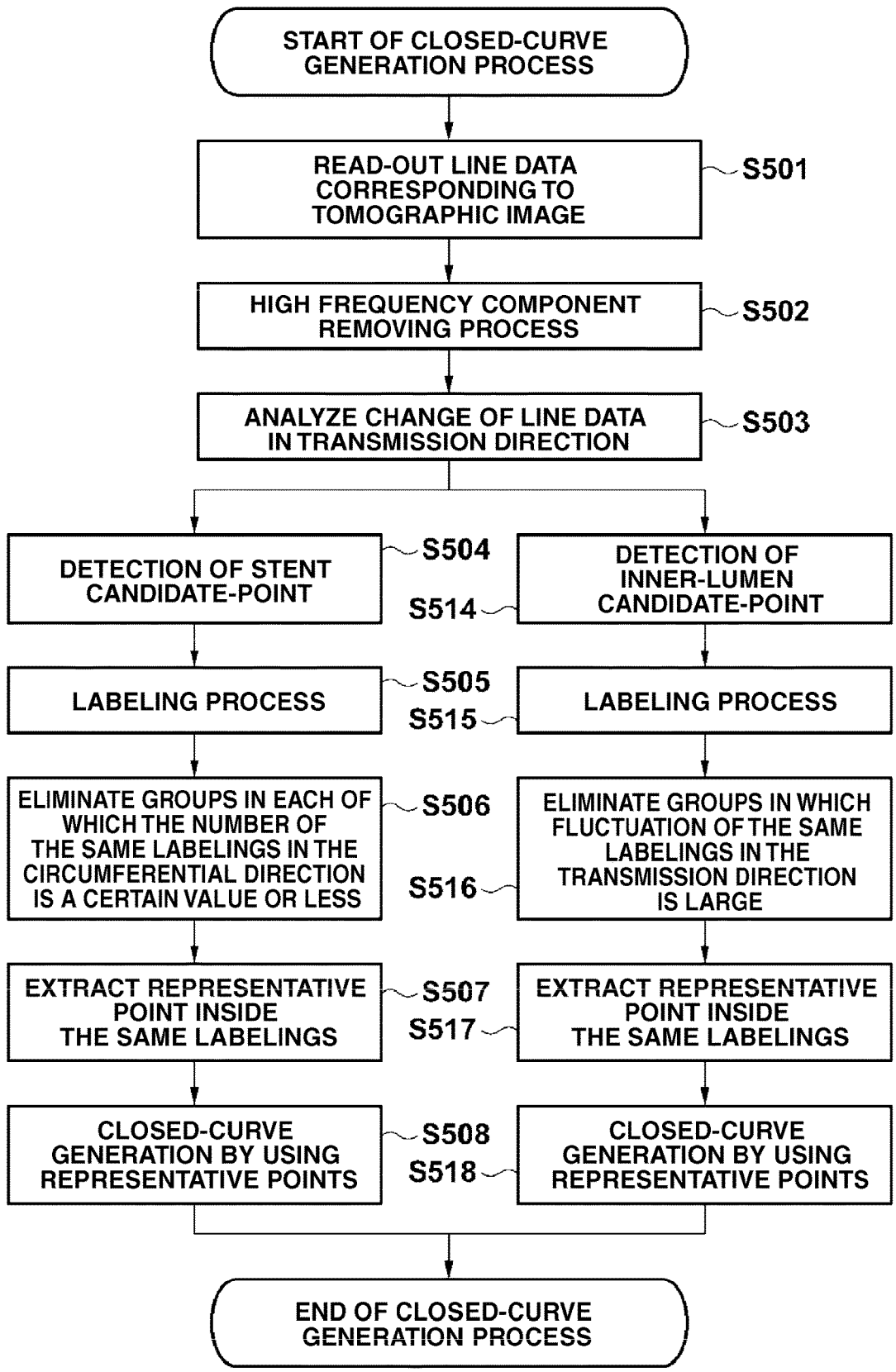
FIG. 5 is a flowchart showing a flow of a closed-curve generation process.

Set forth next with reference to FIG. 5 is an explanation of the flow of the closed-curve generation process carried out by the closed-curve generation unit 307. When a closed-curve generation instruction is inputted from a user through the operation panel 238, the control unit 306 specifies the tomographic image (predetermined tomographic image) which is now displayed on the LCD monitor 217 and, in this situation, instructs the closed-curve generation unit 307 to generate a stent closed-curve and an inner-wall closed-curve for the tomographic image.

In the closed-curve generation unit 307 which received the closed-curve generation instruction from the control unit 306, a closed-curve generation process shown in FIG. 5 starts or is initiated.

In step S501, line data corresponding to the tomographic image specified by the control unit 306 are read-out from the line data memory 302.

In step S502, high frequency components of the read-out line data are removed by using a lowpass filter. Since OFDI generally has high resolution, the generated line data include a lot of spectrum noises. Consequently, in this step, the aforesaid spectrum noises are removed and data suitable for the image processing is generated.

In step S503, change of line data in the transmission direction of the measurement light are analyzed. Specifically, for each of the line data, change of reflection-light intensity in the transmission direction is analyzed and based on the result of that analysis, there are extracted a pixel which becomes a candidate-point of the stent and a pixel which becomes a candidate-point of the inner wall. Thus, the closed-curve generation unit 307 carrying out the operations in steps S501 and S503 is an example of an analysis means for reading-out line data used for construction of a predetermined tomographic image and for analyzing intensity change in transmission direction of the light from the transmission and reception unit for every one of the respective line data. The closed-curve generation unit 307 is also an example of an analysis means for reading-out line data used for constructing a predetermined tomographic image and for analyzing maximum intensity in the transmission direction of light from the transmission and reception unit for every one of the respective line data. calculation means for calculating center position with regard to each labeling group, which was not eliminated by the first elimination means, based on the positional information of each pixel data generation means for generating a stent closed-curve using the center position of the each labeling group, which was calculated by the first calculation means the closed-curve generation unit 307 carrying out the operations in steps S501 and S503 is an example of an analysis meanse closed-curve generation unit 307 can be a computer (e.g., computer installed software, or hardware for exclusive use) appropriately configured o programmed to carry out the operations in steps S501 and S503 (and other steps as discussed below).

Generally, the stent is made of metal, so that in a case in which the transmitted measurement light is illuminated onto the stent surface, approximately all of the measurement light which is illuminated onto the stent surface is reflected and it does not reach the rear side of the stent. On the other hand, the biological tissue is constituted by a fatty material or the like, so that when the transmitted measurement light passes through aperture portions of the mesh of the stent formed in a mesh shape and reaches as far as the inner wall of the biological tissue, the light penetrates through the tissue by being attenuated in accordance with a predetermined attenuation rate. More specifically, in a case in which the measurement light reaches as far as the inner wall, it is possible to receive the rear side scattered light in accordance with the scattering coefficient and the phase function of the biological tissue.

Consequently, with regard to the line data generated based on the measurement light which is illuminated onto the stent surface, the reflection light intensity increases steeply and becomes maximum at the position corresponding to the stent surface in the transmission direction of the measurement light and thereafter, the reflection light intensity decreases steeply on the rear side from the position corresponding to the stent surface.

On the other hand, with regard to the line data generated based on the measurement light reaching as far as the inner wall of the tissue, the reflection light intensity increases steeply and becomes maximum in the vicinity of the position corresponding to the inner wall in the transmission direction of the measurement light and thereafter, the reflection light intensity decreases by a constant rate.

In this embodiment disclosed by way of example, by focusing attention on such a difference in characteristics between a case in which the measurement light is illuminated onto the stent surface and a case in which the light reaches as far as the inner wall, the stent and the inner wall can be distinguished and the stent candidate-point and the inner-wall candidate-point can be detected depending on the respective methods.

Specifically, in step S504, the detection of the aforesaid stent candidate-point is carried out. FIG. 6A is a diagram for explaining a process for detecting a stent candidate-point in step S504. In FIG. 6A, reference numeral 6a indicates a diagram showing an aspect in which each position in the transmission direction of the measurement light (distance from the transmission and reception unit) is arranged on the horizontal axis and a value of each pixel data of line data (intensity of the interference light) is arranged on the vertical axis, and there is plotted each pixel data value of the line data generated based on the measurement light which is illuminated onto the stent surface. The closed-curve generation unit 307 carrying out the operation in step S504 is an example of a detection means for detecting, based on the analysis result in step S503, pixel data expressing stent position in the transmission direction for every one of the respective line data.

As shown in 6a of FIG. 6A, within each pixel data constituting the line data, the pixel data at the position on the outside of the catheter sheath (that is, in the diagnosis target region) repeats minimal change in the transmission direction of the measurement light, increases steeply at the position corresponding to the stent surface and thereafter, decreases steeply. Consequently, in case of calculating average inclination (differential value) in a predetermined length (predetermined length in the transmission direction of the measurement light) for every predetermined distance in the diagnosis target region, there can be obtained a graph such as shown in 6b of FIG. 6A. Consequently, by detecting pixel data at the position at which the differential value exceeds a predetermined threshold value, it is possible to detect a stent candidate-point (see 601).

It is possible for the stent candidate-point to be at the position at which the differential value exceeds the plus threshold value, to be at the position at which the differential value exceeds the minus threshold value or to be at the intermediate position between both of them.

Figure 6B:
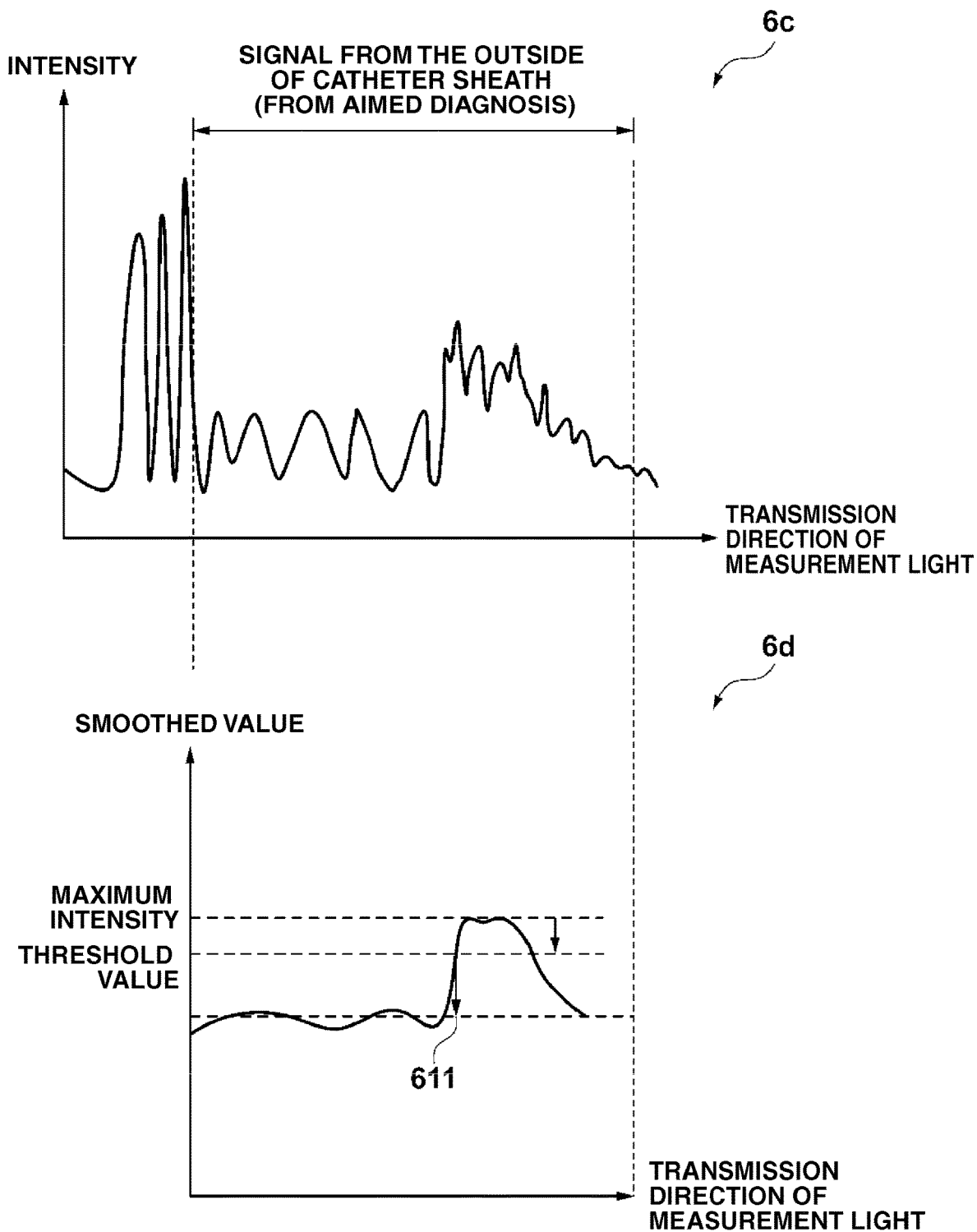
FIG. 6B is a diagram for explaining a general outline of a detection process of an inner-wall candidate-point.

Referring once again to FIG. 5, in step S514, detection of the inner-wall candidate-point is carried out. FIG. 6B is a diagram for explaining a process for detecting an inner-wall candidate-point in step S514. In FIG. 6B, a reference numeral 6c indicates a diagram showing an aspect in which each position in the transmission direction of the measurement light (distance from the transmission and reception unit) is arranged on the horizontal axis and a value of each pixel data of line data (intensity of the interference light) is arranged on the vertical axis, and there is plotted each pixel data value of the line data generated based on the measurement light which reached the inner wall.

The graph identified as 6d in FIG. 6B indicates a diagram obtained by carrying out a smoothing-process for the diagram of 6c. As shown in 6d of FIG. 6B, within each pixel data constituting the line data, the pixel data at the position on the outside of the catheter sheath (that is, in the diagnosis target region) repeats minimal change in the transmission direction of the measurement light, increases steeply in the vicinity of the position corresponding to the inner wall surface, becoming a maximum intensity and thereafter, decreases at a constant rate. Consequently, in the diagnosis target region, it is possible, for the first pixel data at the position intersecting with the intensity which is obtained by subtracting as much as a predetermined intensity value, to be detected as an inner-wall candidate-point (see 611). As indicated by 611 in FIG. 6B, the first pixel data at the position intersecting with the intensity which is obtained by subtracting a predetermined intensity value from the maximum intensity value, is detected as an inner-wall candidate-point. The side of 611 in FIG. 6B is referred to as the near-side.

When stent candidate-points are detected in step S504, after step S505, a stent closed-curve is going to be generated by using the detected stent candidate-points. Similarly, when inner-wall candidate-points are detected in step S514, after step S515, an inner-wall closed-curve is going to be generated by using the detected inner-wall candidate-points. The closed-curve generation unit 307 carrying out the operation in step S514 is an example of a detection means for detecting pixel data expressing inner-wall position of the biological tissue in the transmission direction for every one of the respective line data based on the analysis result by the second analysis means.

First, there will be explained the process for generating a stent closed-curve by using the stent candidate-points.

In step S505, a labeling process is carried out with respect to pixel data of a stent candidate-point in each of the detected line data.

Specifically, if the distance from the transmission and reception unit to the stent candidate-point of the line data of the labeling processing target lies within a predetermined range with respect to the distance from the transmission and reception unit to the stent candidate-point of the adjacent line data (line data on a line which is up (or down) by one line from the line of the labeling processing target), the same label as that of the stent candidate-point on the adjacent line data is added thereto.

On the other hand, in a case in which the distance from the transmission and reception unit to the stent candidate-point of the line data of the labeling processing target does not lie within the predetermined range with respect to the distance from the transmission and reception unit to the stent candidate-point of the adjacent line data, a different label from that of the adjacent line data is added thereto. The closed-curve generation unit 307 carrying out the operation in step S505 is an example of a labeling means for labeling each pixel data expressing the stent position detected for every one of the respective line data based on each positional information.

Figure 7:
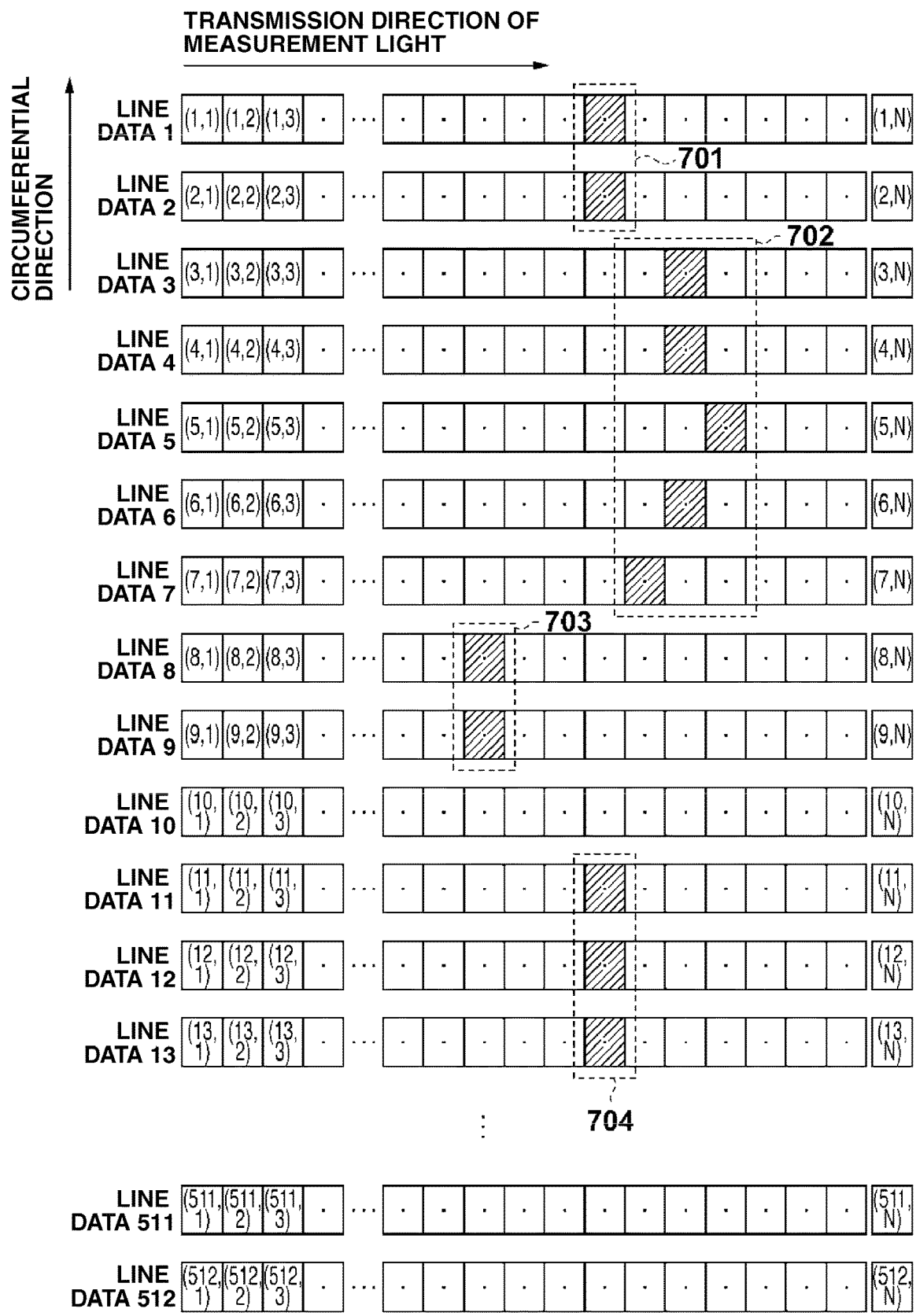
FIG. 7 is a diagram explaining a general outline of a labeling process for stent candidate-points.

FIG. 7 is a diagram showing an aspect in which the labeling process was carried out in step S505 with respect to pixel data of a stent candidate-point in each of the line data detected in step S504.

In FIG. 7, hatched pixel data express pixel data of stent candidate-points. Also, dotted lines surrounding the peripheries of a plurality of stent candidate-points show the fact that the same labels are added to the stent candidate-points included in the aforesaid dotted lines. In the example of FIG.

7, there are shown two labeling groups (labeling groups 701, 703) each of which is composed of two stent candidate-points, one labeling group (labeling group 702) which is composed of five stent candidate-points and one labeling group (labeling group 704) which is composed of three stent candidate-points.

In step S506, there is eliminated the labeling group in which the number of stent candidate-points included in each labeling group (the number of stent candidate-points which are added with the same labels) is a predetermined value or less (equal or less than the length corresponding to the thickness of the stent-mesh) in the circumferential direction. This is because there is a high possibility, for the labeling group in which the number of the stent candidate-points in the circumferential direction is a predetermined value or less, that noise is being detected erroneously as a stent candidate-point. The closed-curve generation unit 307 carrying out the operation in step S506 is an example of an elimination means for eliminating, within respective labeling groups applied with the same labels, labeling groups in which the number of pixel data in the circumferential direction, which is included in one labeling group, is a predetermined value or less.

Figure 8:
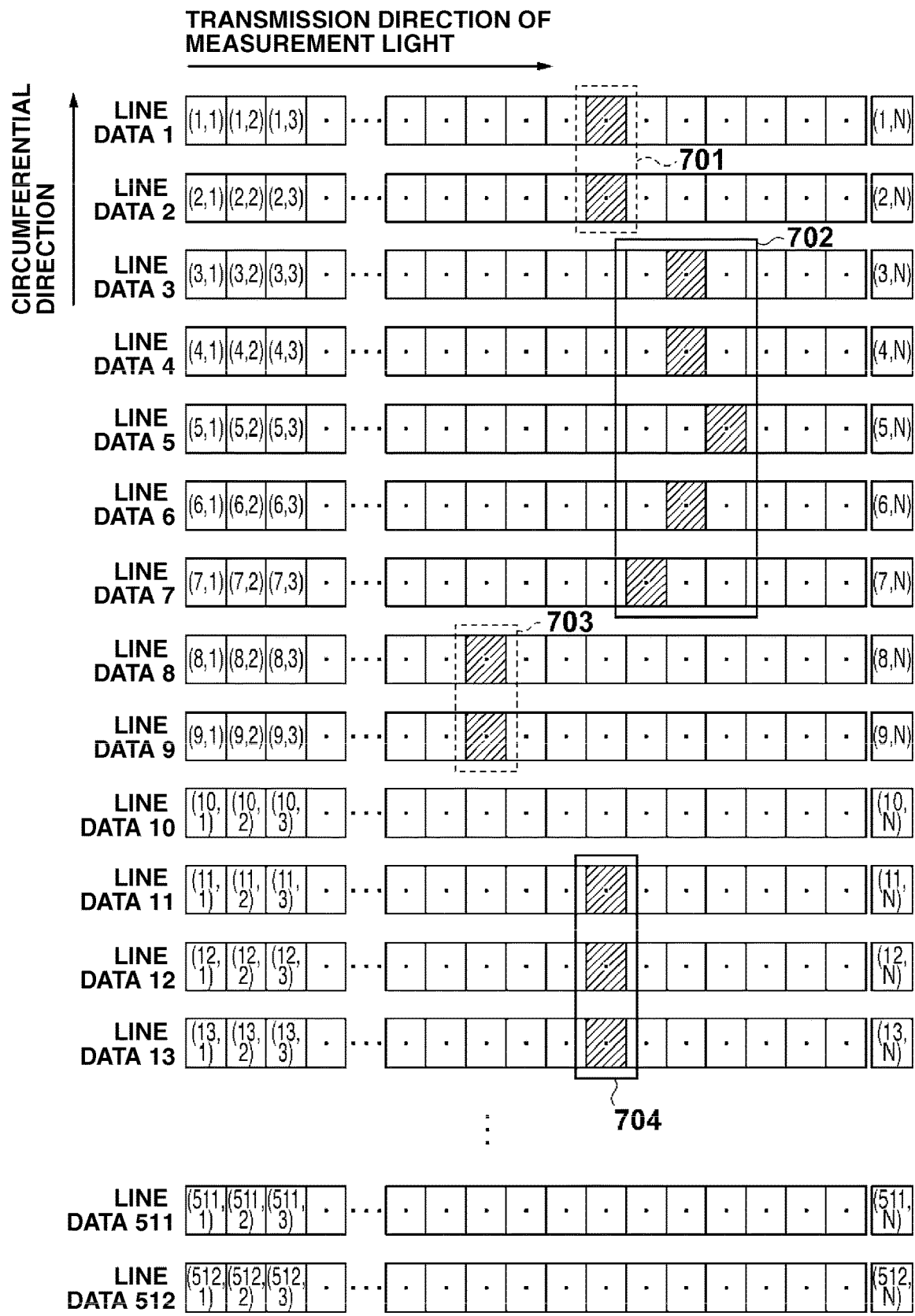
FIG. 8 is a diagram for explaining a general outline of an elimination process of a labeling group having stent candidate-points.

FIG. 8 is a diagram showing an aspect, with respect to the respective labeling groups shown in FIG. 7, in which there were eliminated the labeling groups in each of which the number of stent candidate-points in the circumferential direction, which are added with the same labels, is a predetermined value or less. In the example of FIG. 8, there is shown the fact that a labeling group 701 and a labeling group 703 are eliminated.

In step S507, a representative point is extracted from each labeling group which was not eliminated in step S506. Specifically, for the position of each stent candidate-point included in each labeling group, a mid-value or average-value of the position of each stent candidate-point in the transmission direction of the measurement light and a mid-value or average-value of the position of each stent candidate-point in the circumferential direction are calculated respectively, and these are identified as data of the representative point. However, it is also possible for the position of the stent candidate-point, which presents the mid-value in either one of the transmission direction and the circumferential direction, to be selected as the representative point. The closed-curve generation unit 307 carrying out the operation in step S507 is an example of a calculation means for calculating center position with regard to each labeling group, which was not eliminated, based on the positional information of each pixel data.

Figure 9:
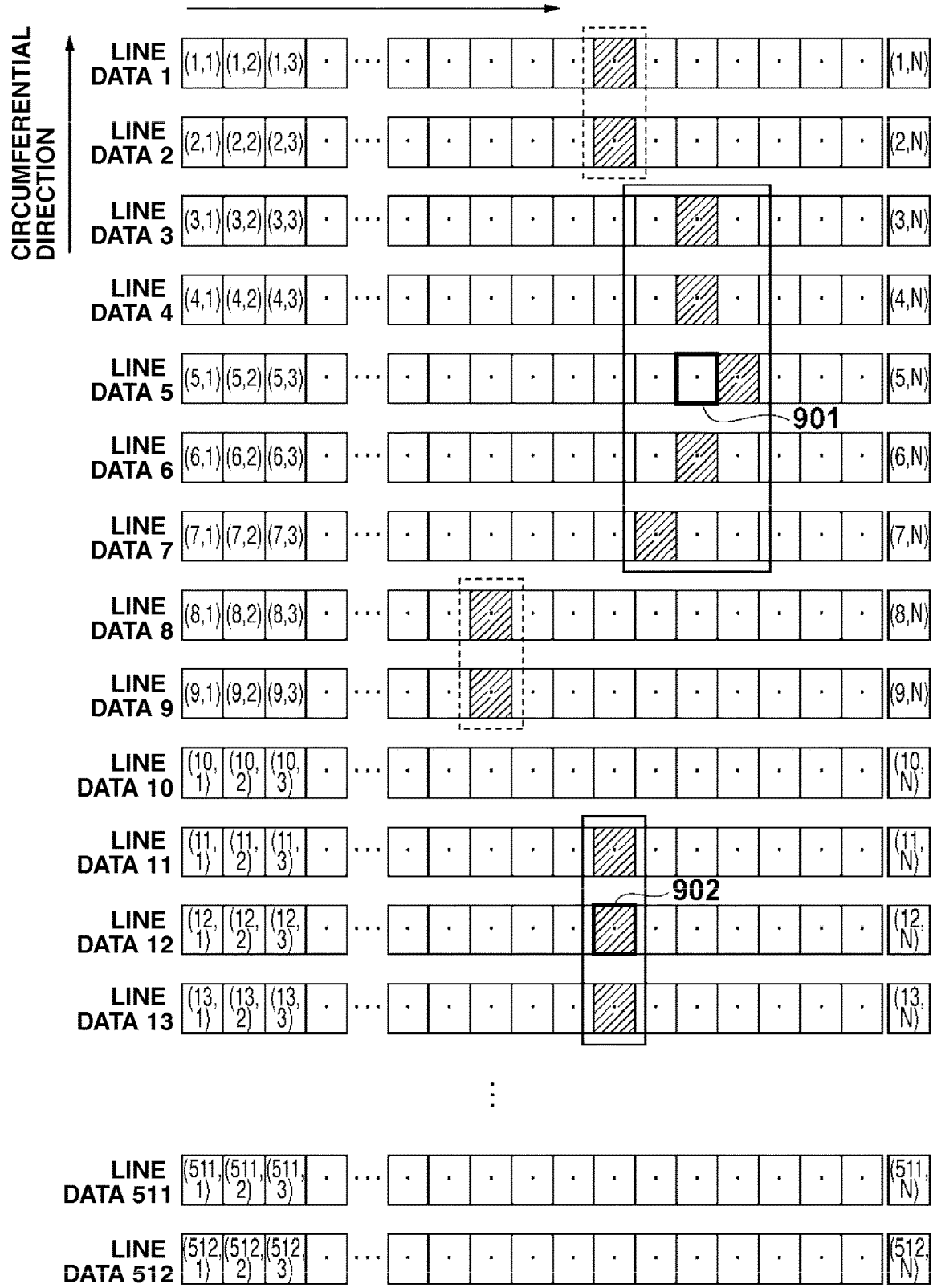
FIG. 9 is a diagram for explaining a general outline of an extraction process of a representative point in a labeling group having stent candidate-points.

FIG. 9 shows an aspect in which representative points are extracted from the labeling groups 702 and 704 which were not eliminated in step S506. In the example of FIG. 9, the labeling group 702 is constituted by pixel data including five stent candidate-points (pixel data including stent candidate-points from lines 3 to 7 and pixel data having fluctuation for three pixels in the measurement light transmission direction). Consequently, a pixel 901 is extracted as the representative point from the labeling group 702. Similarly, a pixel 902 is extracted as the representative point from the labeling group 704.

In step S508, a stent closed-curve is generated by using the representative points extracted in step S507. Thus, the closed-curve generation unit 307 carrying out the operation in step S508 is an example of a generation means for generating a stent closed-curve using the center position of the each labeling group, which was calculated by the closed-curve generation unit 307 in step S507.

In this manner, in the optical imaging apparatus for diagnosis relating to this embodiment, there is employed a constitution or configuration wherein the case in which the number of the stent candidate-points included in one labeling group is a predetermined number or less in the circumferential direction is judged to be noise and is excluded from the calculation target of the closed curve, and wherein with regard to the remaining respective labeling groups, representative points are extracted and the closed curve is generated using the extracted representative points. As a result, it becomes possible to generate a closed curve in which the shape of the stent indwelled inside the biological tissue is reproduced more precisely.

Next, there will be explained the process for generating an inner-wall closed-curve by using inner-wall candidate-points. In step S515, a labeling process is carried out with respect to pixel data of an inner-wall candidate-point in each line data, which was detected. The closed-curve generation unit 307 carrying out the operation in step S515 is an example of a labeling means for labeling each pixel data expressing the inner-wall position detected for every one of the respective line data based on each positional information.

Specifically, if the distance from the transmission and reception unit to the inner-wall candidate-point of the line data of the labeling processing target lies within a predetermined range with respect to the distance from the transmission and reception unit to the inner-wall candidate-point of the adjacent line data (line data on a line which is up (or down) by one line from the line of the labeling processing target), the same label as that of the inner-wall candidate-point on the adjacent line data is added thereto. However, in a case in which the stent does not exist in the obtained tomographic image, the inner-wall candidate-point is extracted from all line data and it becomes a situation in which only one label is attached. In order to avoid this situation, a certain upper limit is provided for the number of lines in the labeling group beforehand and the same label is added thereto if it is within the upper limit thereof. Also, it is possible for the label to be added for every line number from the very beginning.

On the other hand, in a case in which the distance from the transmission and reception unit to the stent candidate-point of the line data of the labeling processing target does not lie within the predetermined range with respect to the distance from the transmission and reception unit to the stent candidate-point of the adjacent line data or in a case in which the number of lines in the same label exceeds the upper limit, a different label from that of the adjacent line data is added thereto.

Figure 10:
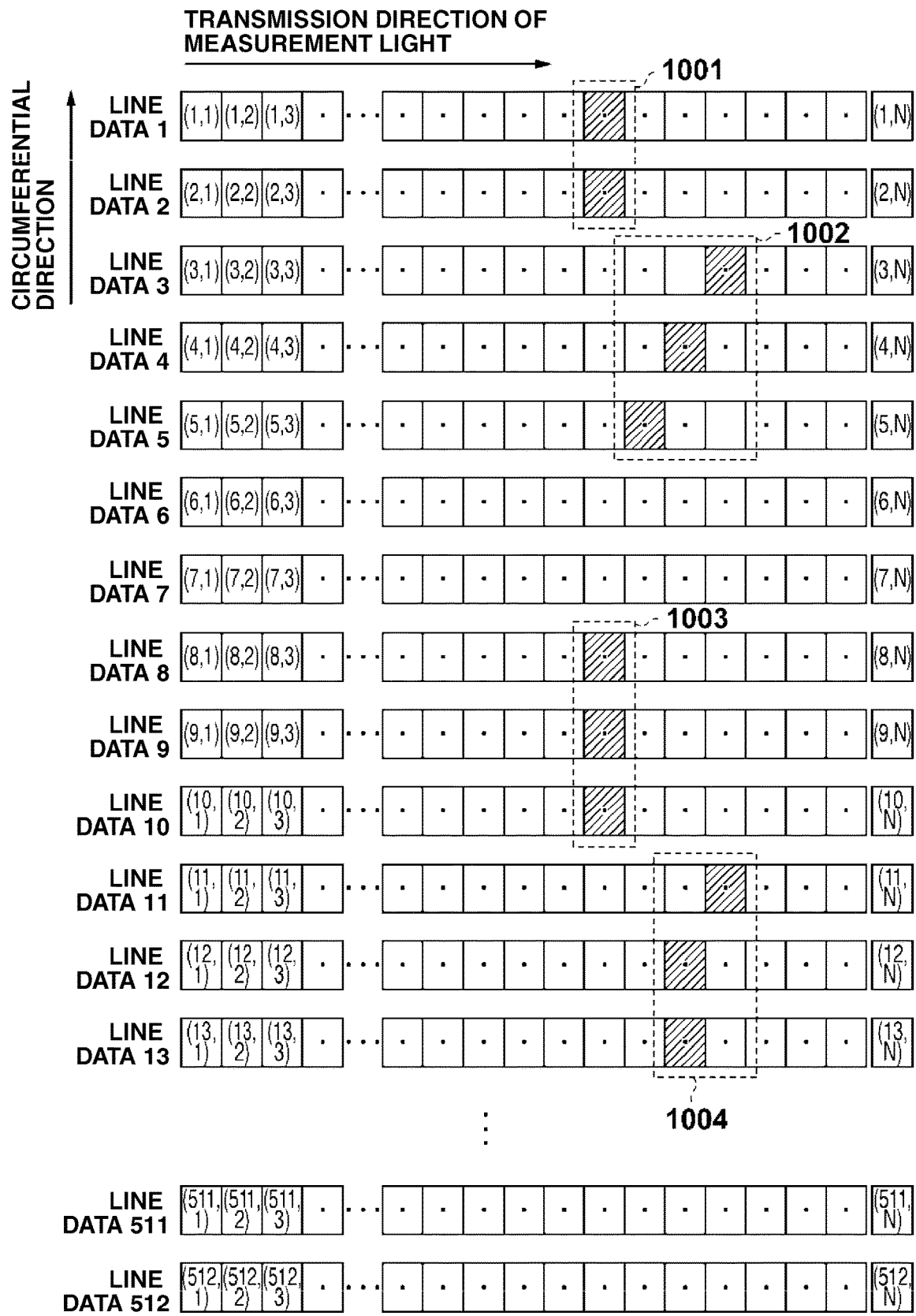
FIG. 10 is a diagram for explaining a general outline of a labeling process for inner-wall candidate-points.

FIG. 10 is a diagram showing an aspect in which the labeling process was carried out in step S515 with respect to pixel data of an inner-wall candidate-point in each of the line data detected in step S514.

In FIG. 10, cross-hatched pixel data express or identify pixel data of inner-wall candidate-points. Also, dotted lines surrounding the peripheries of a plurality of inner-wall candidate-points show the fact that the same labels are added to the inner-wall candidate-points included in such dotted lines. In an example of FIG. 10, there are shown one labeling group (labeling group 1001) which is composed of two inner-wall candidate-points and three labeling groups (labeling groups 1002 to 1004) each of which is composed of three inner-wall candidate-points.

Figure 11:
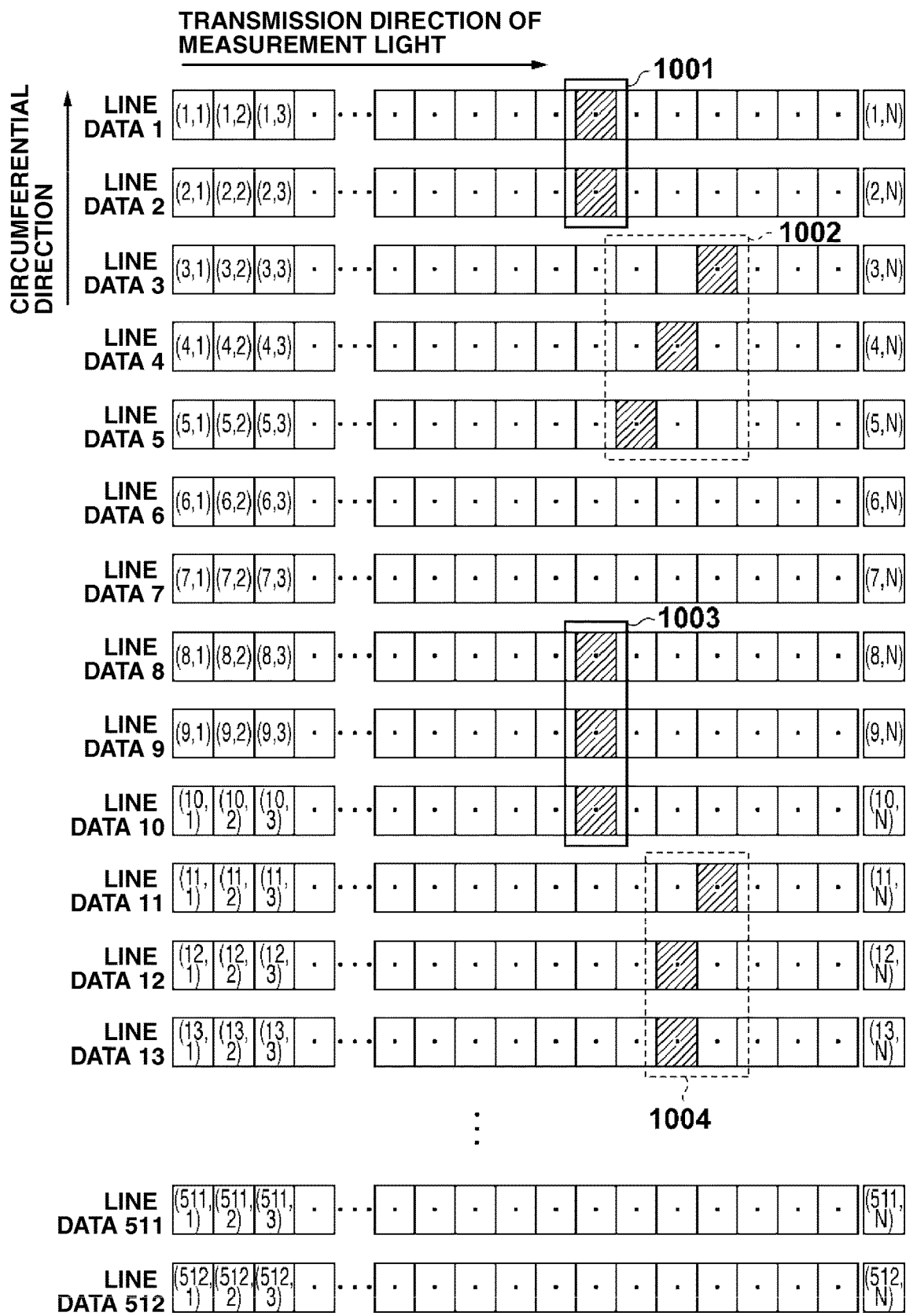
FIG. 11 is a diagram for explaining a general outline of an elimination process of a labeling group having inner-wall candidate-points.

In step S516, fluctuation in the transmission direction of the measurement light for the inner-wall candidate-points (inner-wall candidate-points to which the same labels are added) which are included in each labeling group is found-out or determined; the aforesaid found-out fluctuation is compared with that of the adjacent labeling group; and the labeling group on the side in which the fluctuation is large is eliminated (the term "large" refers to the fluctuation in the distance from the transmission and reception unit to the inner-wall candidate-point of the line data of the labeling processing target in each of the labeling groups ranging or varying widely; for example, the fluctuation of the group 1002 in FIG. 11 is "large" compared to that of the group 1001). This is because there is a high possibility, for the labeling group on the side in which the fluctuation in the transmission direction is large, that noises are to be detected erroneously as inner-wall candidate-points. The closed-curve generation unit 307 carrying out the operation in step S516 is an example of an elimination means for eliminating a labeling group in which the fluctuation of pixel data, included in one labeling group within the respective labeling groups applied with the same labels by the second labeling means, in the transmission direction is large.

FIG. 11 is a diagram showing an aspect in which the fluctuation in the transmission direction of the inner-wall candidate-points, for which the same labels are added with respect to the respective labeling groups shown in FIG. 10, is found-out or determined; the aforesaid found-out fluctuation is compared with that of the adjacent labeling group; and the labeling group on the side in which the fluctuation is large was eliminated. In the example of FIG. 11, there is shown the fact that the labeling group 1002 and the labeling group 1004 are eliminated.

In step S517, a representative point is extracted from each labeling group which was not eliminated in step S516. Specifically, for the position of each inner-wall candidate-point included in each labeling group, a mid-value or average-value of the position of each inner-wall candidate-point in the transmission direction of the measurement light and a mid-value or average-value of the position of each inner-wall candidate-point in the circumferential direction are calculated respectively, and these are identified as data of the representative point. However, it is also possible for the position of the inner-wall candidate-point, which presents the mid-value in either one of the transmission direction and the circumferential direction, to be selected as the representative point. The closed-curve generation unit 307 carrying out the operation in step S517 is an example of a calculation means for calculating, with regard to each labeling group, which was not eliminated by the closed-curve generation unit 307, center position based on positional information of each pixel data.

Figure 12:
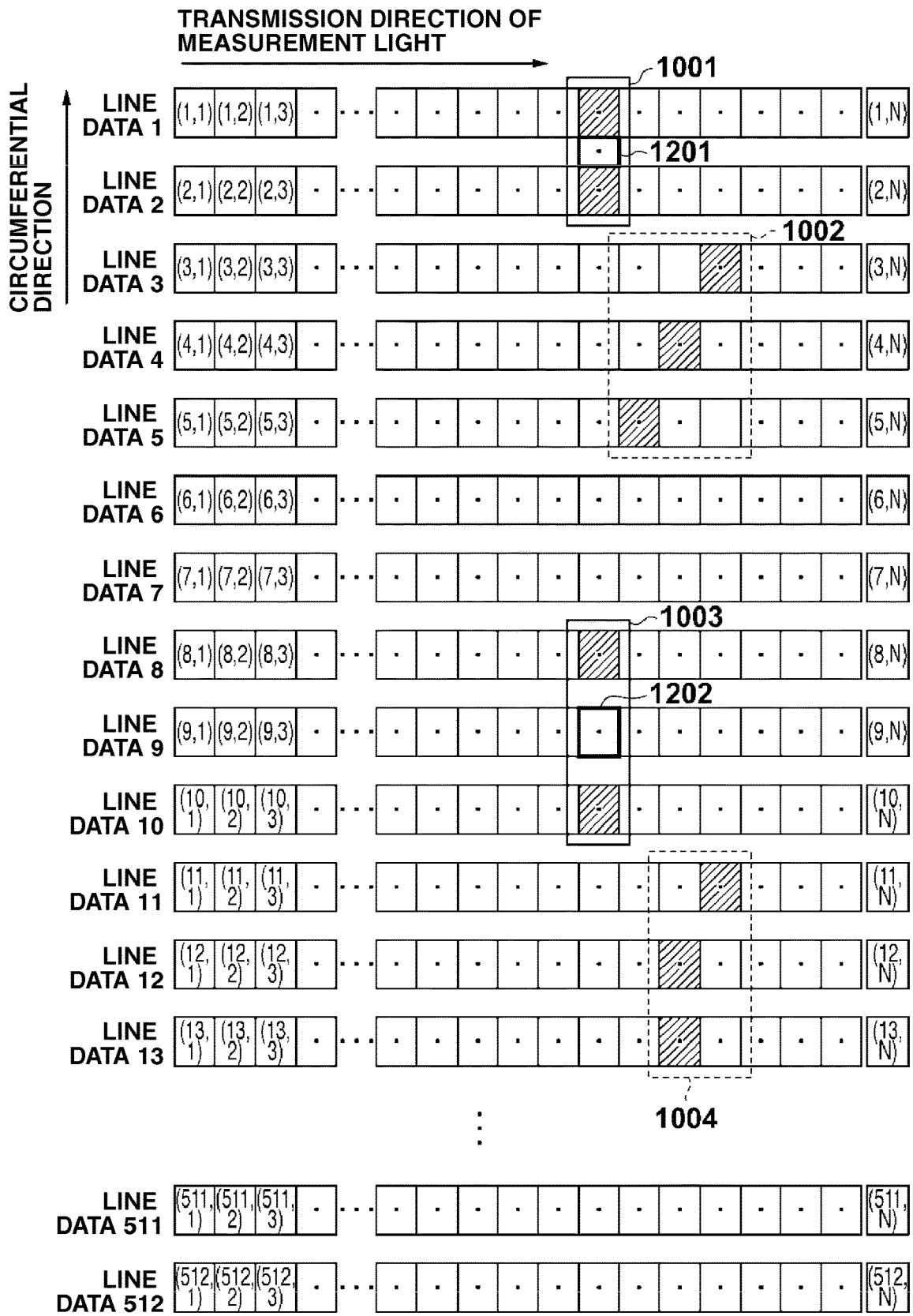
FIG. 12 is a diagram for explaining a general outline of an extraction process of a representative point in a labeling group having inner-wall candidate-points.

FIG. 12 shows an aspect in which representative points are extracted from the labeling groups 1001 and 1003 which were not eliminated in step S516. In the example of FIG. 12, the labeling group 1001 is constituted by pixel data including two inner-wall candidate-points (pixel data including inner-wall candidate-points from lines 1 and 2 and pixel data having fluctuation for one pixel in the measurement light transmission direction). Consequently, a pixel 1201 is extracted or selected (e.g., through line addition-averaging) as the representative or candidate point from the labeling group 1001. Similarly, a pixel 1202 is extracted as the representative point from the labeling group 1003.

In step S518, an inner-wall closed-curve is generated by using the representative points extracted in step S517. The closed-curve generation unit 307 carrying out the operation in step S518 is an example of a generation means for generating a closed-curve of the inner wall by using the center position of each labeling group which was calculated.

In this manner, in the optical imaging apparatus for diagnosis relating to this embodiment disclosed by way of example, there is employed a constitution or configuration wherein the case in which the fluctuation of the inner-wall candidate-points included in one labeling group is large in the transmission direction is judged as a noise case and is excluded from the calculation target of the closed curve, and wherein with regard to the remaining respective labeling groups, representative points are to be extracted and the closed curve is to be generated by using the extracted representative points. As a result thereof, it becomes possible to generate a closed curve in which the shape of the inner wall is reproduced relatively precisely even in a state in which the stent is indwelled inside the biological tissue.

6. Embodiment

Next, according to the closed-curve generation process shown in FIG. 5, there will be explained an embodiment in the case of generating a stent closed-curve and an inner-wall closed-curve of a biological tissue from a tomographic image.

Figure 13:
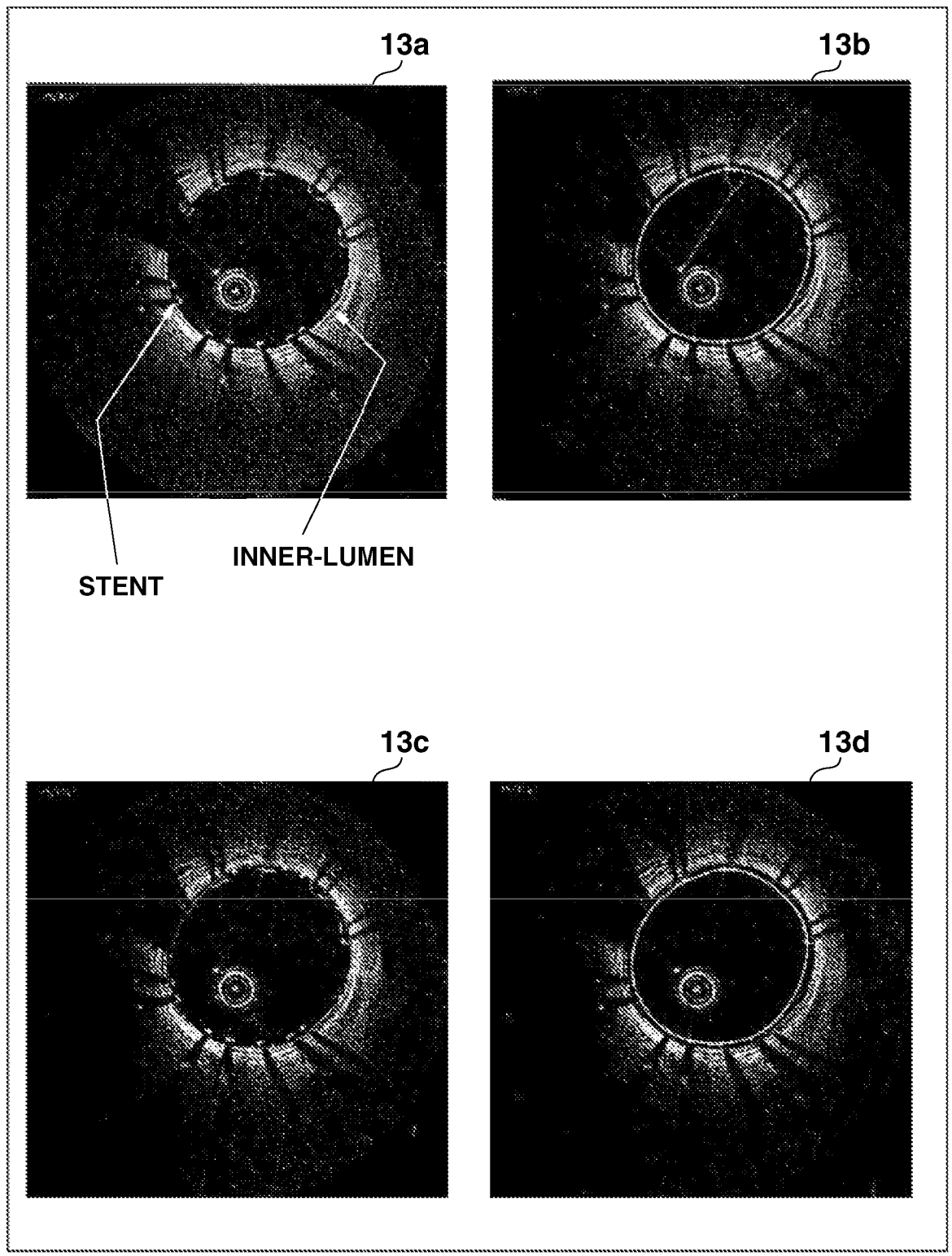
FIG. 13 is a diagram showing a stent closed-curve and an inner-wall closed-curve that have been generated and displayed.

FIG. 13 is a diagram showing an aspect in which a stent closed-curve and an inner-wall closed-curve are generated and displayed according to the closed-curve generation process shown in FIG. 5.

In FIG. 13, the image identified as 13*a* shows one example of a tomographic image used for a closed-curve generation process, and the image identified as 13*b* shows a stent closed-curve which is generated by applying a stent closed-curve generation process with respect to the tomographic image shown in 13*a*. Also, the image identified as 13*c* shows an inner-wall closed-curve which is generated by applying an inner-wall closed-curve generation process with respect to the tomographic image shown in 13*a*. Further, the image identified as 13*d* shows an aspect in which the stent closed-curve shown in 13*b* and the inner-wall closed-curve shown in 13*c* are displayed by being superimposed.

As shown by the images identified as 13*b* and 13*c*, according to the closed-curve generation process relating to this embodiment, it becomes possible, with regard to the stent and the inner wall of the biological tissue, to generate the closed curves which reproduce the shapes of the stent and the inner wall of the biological tissue more precisely.

As clear from the explanation above, in the optical imaging apparatus for diagnosis relating to this embodiment, there is employed a constitution or configuration which focuses attention on the fact that the intensity changes of the line data are different between a case in which the measurement light is illuminated on the stent and a case in which the measurement light reaches the inner wall of the biological tissue, wherein the constitution or configuration carries out processes suitable for the respective detections of the stent and the inner wall of the biological tissue. Thus, it became possible to discriminate the stent and the inner wall more clearly.

Also, there is employed a constitution in which a labeling process is carried out with respect to the stent candidate-points and the inner-wall candidate-points and in which in light of the characteristics of the stent candidate-point and the inner-wall candidate-point, a labeling group which is judged to be detected erroneously is eliminated and after this situation, the closed curve is to be generated. Thus, it became possible to generate closed curves which reproduce the shapes of the stent and the inner wall precisely.

Second Embodiment

In the above-described first embodiment, there was employed a configuration in which the shape of the indwelled stent and the shape of the inner wall of the biological tissue at the indwelling position of the stent are reproduced more precisely. As a result, it became possible to comprehend the positional relationship between the stent and the inner wall more accurately.

Here, due to the fact that there exists a certain amount of thickness for the actual stent, there is only reproduced the reflection surface for the stent displayed on the tomographic image and it is not possible yet to reproduce the accurate thickness of the stent. For this reason, even in a case in which there exists an observed gap between the stent and the inner-wall on the tomographic image, it is not possible to judge whether a gap actually exists between the stent and the inner wall of the tissue or whether the gap is actually caused by the stent-thickness.

This second embodiment makes it possible to confirm the thickness of the indwelled stent on the tomographic image. Hereinafter, there will be explained an optical imaging apparatus for diagnosis relating to this second embodiment. The following description focuses primarily on differences between this second embodiment and the embodiment described earlier, and features in this second embodiment that are the same as in the first embodiment are designated by like reference numerals and a detailed description of such features is not repeated.

1. Functional Constitution of Signal Processing Unit

Figure 14:
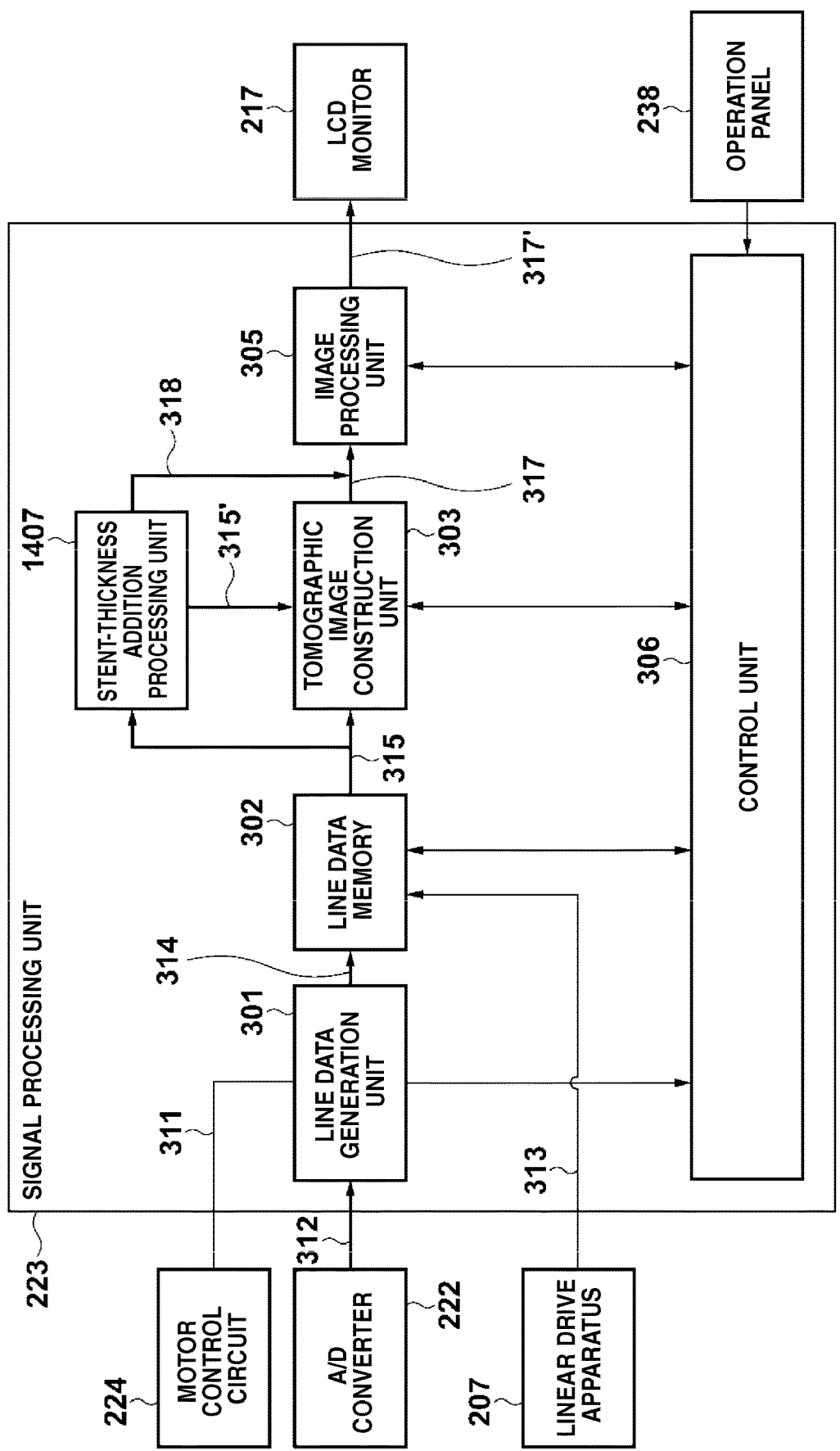
FIG. 14 is a diagram showing a functional constitution of a signal processing unit.

First, there will be explained a functional constitution or configuration of a signal processing unit 223 of an optical imaging apparatus for diagnosis 100 relating to this second embodiment. FIG. 14 is a diagram showing a functional constitution or configuration of the signal processing unit 223 for realizing a construction process of a tomographic image and a stent-thickness display process based on the line data utilized for the construction of the above-described tomographic image.

As shown in FIG. 14, interference light data generated in an A/D converter 222 is processed, in a line data generation unit 301 inside the signal processing unit 223, such that the number of lines per one rotation of the radial scanning motor will become 512 by using a signal of an encoder unit 206 of a radial scanning motor 205, which is outputted from a motor control circuit 224.

It is assumed, as one example here, that the tomographic image is to be constructed from 512 lines, but the invention here is not limited by this number of the lines.

Line data 314 outputted from the line data generation unit 301 are stored in a line data memory 302 for every one rotation of the radial scanning motor based on instruction from a control unit 306. At that time, in the control unit 306, a pulse signal 313 outputted from a moving amount detector of a linear drive apparatus 207 is counted beforehand and when storing the line data 314 into the line data memory 302, the data are stored by being correlated with the count value when generating each of the line data 314.

The above description explained that the line data memory 302 is arranged and the line data 314 is stored by correlating it with the count value of the pulse signal 313 outputted from the moving amount detector of the linear drive apparatus 207, but the invention is not limited by this aspect. For example, it is possible that a tomographic image data memory is arranged behind the tomographic image construction unit 303 and the tomographic image 317 is stored in such a manner as to be correlated with the count value of the pulse signal 313 outputted from the moving amount detector of the linear drive apparatus 207.

Referring once again to FIG. 14, based on the instruction from the control unit 306, the line data 315 stored by being correlated with the count value is subjected to various kinds of processes (line addition-averaging process, filtering process and the like) in the tomographic image construction unit 303 and thereafter, is sequentially outputted as tomographic image 317 by being Rθ-converted.

Further, in the image processing unit 305, image processing for displaying on the LCD monitor 217 is applied and thereafter, it is outputted to the LCD monitor 217 as a tomographic image 317'.

Also, the line data 315 stored by being correlated with the count value is read into a stent-thickness addition processing unit 1407 based on the instruction from the control unit 306, and there are executed an addition process of an indicator which expresses the stent-thickness and a generation process of a closed-curve which expresses the inner-wall position (these are collectively referred to as stent-thickness display process). Line data 315' added with the indicator are inputted to the tomographic image construction unit 303 and the tomographic image 317 is reconstructed. Also, inner-wall closed-curve data 318 are inputted to the image processing unit 305 and are superimposed to the reconstructed tomographic image 317. Details of the stent-thickness display process in the stent-thickness addition processing unit 1407 will be described later.

In the LCD monitor 217, the tomographic image 317' processed in the image processing unit 305 is displayed. Also, in a case in which a stent-thickness display instruction is inputted by a user through the operation panel 238, there is displayed a tomographic image 317' which is constructed based on the line data 315' added with the indicator in the stent-thickness addition processing unit 1407 and which is superimposed with the closed-curve.

2. Flow of Stent-Thickness Display Process

Figure 15:
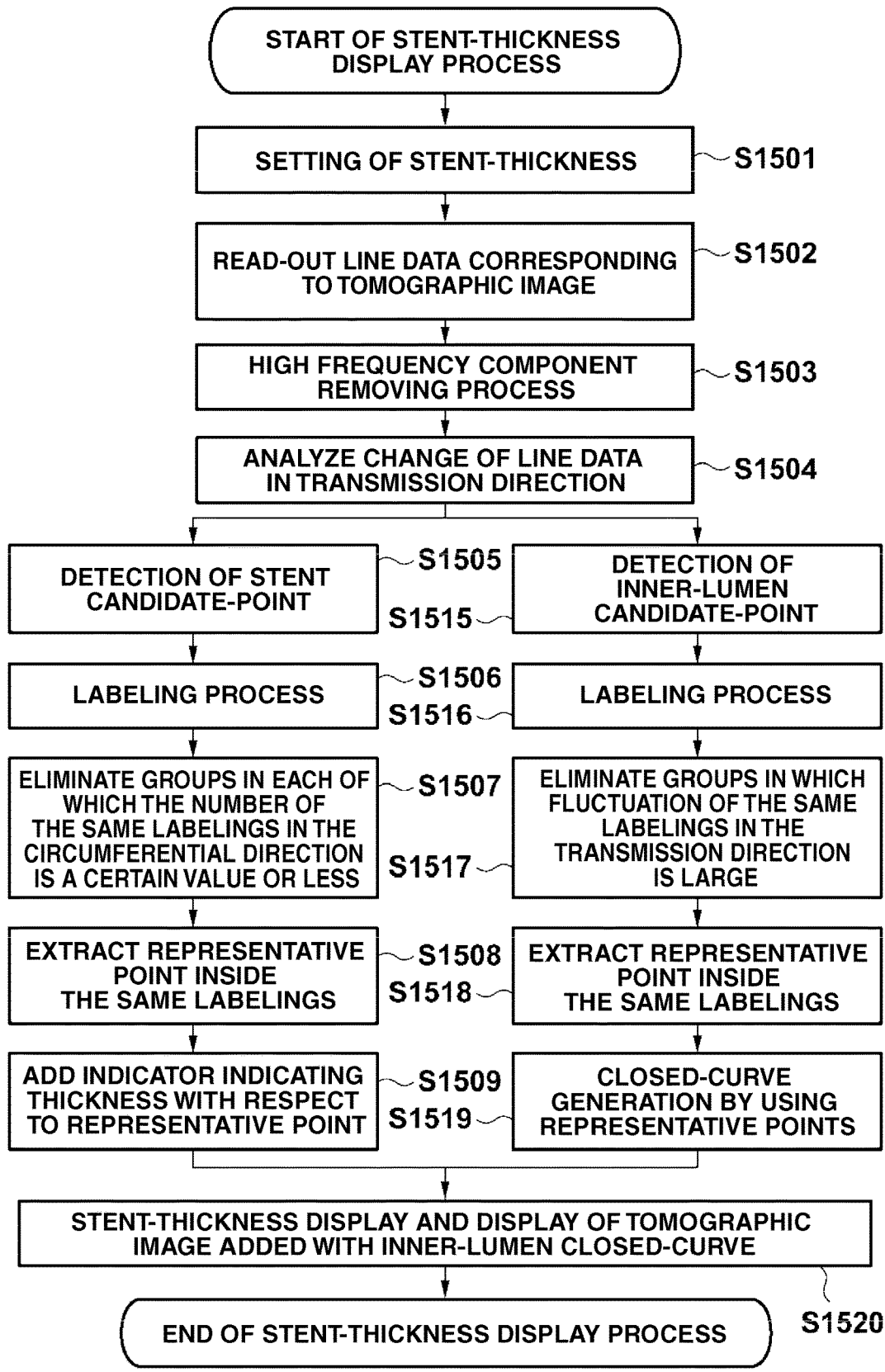
FIG. 15 is a flowchart showing a flow of a display process of stent-thickness.

Set forth next with reference to FIG. 15 is an explanation of a flow of the stent-thickness display process in the stent-thickness addition processing unit 1407.

When the stent-thickness display instruction is inputted by the user through the operation panel 238, there is carried out, in the control unit 306, an instruction to generate an indicator indicating the thickness of the stent and an inner-wall closed-curve with respect to the stent-thickness addition processing unit 1407 in a situation after specifying a tomographic image which is displayed on the LCD monitor 217 at present.

In the stent-thickness addition processing unit 1407 which received the generation instruction of the indicator indicating the stent-thickness and of the inner-wall closed-curve from the control unit 306, the stent-thickness display process shown in FIG. 15 is started.

In step S1501, information relating to the stent-thickness, which is inputted by the user through the operation panel 238, is set.

In step S1502, line data corresponding to the tomographic image, which is specified by the control unit 306, are read-out from the line data memory 302.

In step S1503, high-frequency components of the read-out line data are removed by using a lowpass filter. Generally, an SS-OCT has high-resolution, so that there are included a lot of spectrum noises in the generated line data. Consequently, in this step, the spectrum noises are removed and data suitable for the image processing are generated.

In step S1504, changes of line data in the transmission direction of the measurement light are analyzed. Specifically, in each of the line data, the intensity change of the reflection light in the transmission direction is analyzed and based on the analyzed result of the reflection light, a pixel which becomes a candidate-point of the stent and a pixel which becomes a candidate-point of the inner-wall are extracted.

Generally, the stent is made of metal, so that in a case in which the transmitted measurement light is illuminated onto the stent surface, approximately all of the measurement light which is illuminated onto the stent surface is reflected and it does not reach the rear side of the stent. On the other hand, the inner-wall is constituted by a fatty material or the like, so that when the transmitted measurement light passes through aperture portions of the mesh of the stent formed in a mesh shape and reaches as far as the inner-wall, the light penetrates therethrough by being attenuated in accordance with a predetermined attenuation rate. More specifically, in a case in which the measurement light reaches as far as the inner-wall, it is possible to receive the rear side scattered light in accordance with the scattering coefficient and the phase function of the inner-wall.

Consequently, with regard to the line data generated based on the measurement light which is illuminated onto the stent surface, the reflection light intensity increases steeply and becomes maximum at the position corresponding to the stent surface in the transmission direction of the measurement light and thereafter, it decreases steeply on the rear side from the position corresponding to the stent surface.

On the other hand, with regard to the line data generated based on the measurement light reaching as far as the inner-wall, the reflection light intensity increases steeply and becomes maximum in the vicinity of the position corresponding to the inner-wall in the transmission direction of the measurement light and thereafter, it decreases by a constant rate.

In this embodiment, there will be discussed an example in which by focusing attention on such a difference in characteristics between a case in which the measurement light is illuminated onto the stent surface and a case in which the light reaches as far as the inner-wall, the stent and the inner-wall are distinguished and the stent candidate-point and the inner-wall candidate-point are detected depending on the respective methods, but the detection method of the stent candidate-point is not limited by that aspect.

Specifically, in step S1505, the detection of a stent candidate-point is carried out. The already-described FIG. 6A is a diagram for explaining the process for detecting a stent candidate-point in step S1505. In FIG. 6A, a reference numeral 6a indicates a diagram showing an aspect in which each position in the transmission direction of the measurement light (distance from the transmission and reception unit) is arranged on the horizontal axis and a value of each pixel data of line data (intensity of the interference light) is arranged on the vertical axis, and there is plotted each pixel data value of the line data generated based on the measurement light which is illuminated onto the stent surface.

As shown in the reference numeral 6a of FIG. 6A, within each pixel data constituting the line data, the pixel data at the position on the outside of the catheter sheath (that is, in the diagnosis target region) repeats minimal change in the transmission direction of the measurement light, increases steeply at the position corresponding to the stent surface and thereafter, decreases steeply. Consequently, in case of calculating average inclination (differential value) in a predetermined length (predetermined length in the transmission direction of the measurement light) for every predetermined distance in the diagnosis target region, there can be obtained a graph such as shown in a reference numeral 6b of FIG. 6A. Consequently, by detecting pixel data at the position at which the differential value exceeds a predetermined threshold value, it is possible to detect a stent candidate-point (see 601).

It is possible for the stent candidate-point to be at the position at which the differential value exceeds the plus threshold value, to be at the position at which the differential value exceeds the minus threshold value or to be at the intermediate position between both the plus threshold value and the minus threshold value.

On the other hand, in step S1515, the inner-wall candidate-point is detected. The already-described FIG. 6B is a diagram for explaining a process for detecting an inner-wall candidate-point in step S1515. In FIG. 6B, a reference numeral 6c indicates a diagram showing an aspect in which each position in the transmission direction of the measurement light (distance from the transmission and reception unit) is arranged on the horizontal axis and a value of each pixel data of line data (intensity of the interference light) is arranged on the vertical axis, and there is plotted each pixel data value of the line data generated based on the measurement light which reached the inner-wall.

The diagram identified as 6d in FIG. 6B indicates a diagram obtained by carrying out a smoothing-process for the diagram of 6c. As shown in the diagram identified as 6d in FIG. 6B, within each pixel data constituting the line data, the pixel data at the position on the outside of the catheter sheath (that is, in the diagnosis target region) repeats minimal change in the transmission direction of the measurement light, increases steeply in the vicinity of the position corresponding to the inner-wall surface, becoming a maximum intensity and thereafter, decreases at a constant rate. Consequently, in the diagnosis target region, it is possible, for the first pixel data at the position intersecting with the intensity which is obtained by subtracting as much as a predetermined intensity value from the maximum intensity value, to be detected as an inner-wall candidate-point (see 611).

When stent candidate-points are detected in step S1505, after steps S1506, A1507 and S1508, a process for adding an indicator which expresses the stent-thickness is carried out by using the detected stent candidate-points. On the other hand, when inner-wall candidate-points are detected in step S1515, after steps S1516, S1517 and S1518 a process for generating an inner-wall closed-curve is carried out by using the aforesaid detected inner-wall candidate-points.

First, there will be explained a process for adding an indicator showing the stent-thickness by using a stent candidate-point.

In step S1506, a labeling process is carried out with respect to pixel data of a stent candidate-point in each of the detected line data.

Specifically, if the distance from the transmission and reception unit to the stent candidate-point of the line data of the labeling processing target lies within a predetermined range with respect to the distance from the transmission and reception unit to the stent candidate-point of the adjacent line data (line data on a line which is up by one line from the line of the labeling processing target), the same label as that of the stent candidate-point on the adjacent line data is added thereto.

On the other hand, in a case in which the distance from the transmission and reception unit to the stent candidate-point of the line data of the labeling processing target does not lie within the predetermined range with respect to the distance from the transmission and reception unit to the stent candidate-point of the adjacent line data, a different label from that of the adjacent line data is added thereto.

The already-described FIG. 7 is a diagram showing an aspect in which the labeling process was carried out in step S1506 with respect to pixel data of a stent candidate-point in each of the line data detected in step S1505.

In FIG. 7, cross-hatched pixel data express pixel data of stent candidate-points. Also, dotted lines surrounding the peripheries of a plurality of stent candidate-points show that the same labels are added to the stent candidate-points included in the aforesaid dotted lines. In the example of FIG. 7, there are shown two labeling groups (labeling groups 701, 703) each of which is composed of two stent candidate-points, one labeling group (labeling group 702) which is composed of five stent candidate-points and one labeling group (labeling group 704) which is composed of three stent candidate-points.

In step S1507, there is eliminated the labeling group in which the number of stent candidate-points included in each labeling group (the number of stent candidate-points which are added with the same labels) is a predetermined value or less (equal or less than the length corresponding to the thickness of the stent-mesh) in the circumferential direction. This is because there is a high possibility, for the labeling group in which the number of the stent candidate-points in the circumferential direction is a predetermined value or less, that a noise is to be detected erroneously as a stent candidate-point.

The already-described FIG. 8 is a diagram showing an aspect, with respect to the respective labeling groups shown in FIG. 7, in which there were eliminated the labeling groups in each of which the number of stent candidate-points in the circumferential direction, which are added with the same labels, is a predetermined value or less. In the example of FIG. 8, there is shown that a labeling group 701 and a labeling group 703 are eliminated.

In step S1508, a representative point is extracted from each labeling group which was not eliminated in step S1506. Specifically, for the position of each stent candidate-point included in each labeling group, a mid-value or average-value of the position of each stent candidate-point in the transmission direction of the measurement light and a mid-value or average-value of the position of each stent candidate-point in the circumferential direction are calculated respectively, and these are made to be data of the representative point (that is, the center position is found-out based on the positional information in the transmission direction and the circumferential direction of the stent candidate-point and this is made to be the representative point).

Further, in step S1509, the data are changed to an indicator indicating the stent-thickness, with regard to the pixel data for every number of pixels corresponding to the set stent-thickness, from the center position found in step S1508 toward the transmission direction of the measurement light.

Figure 16:
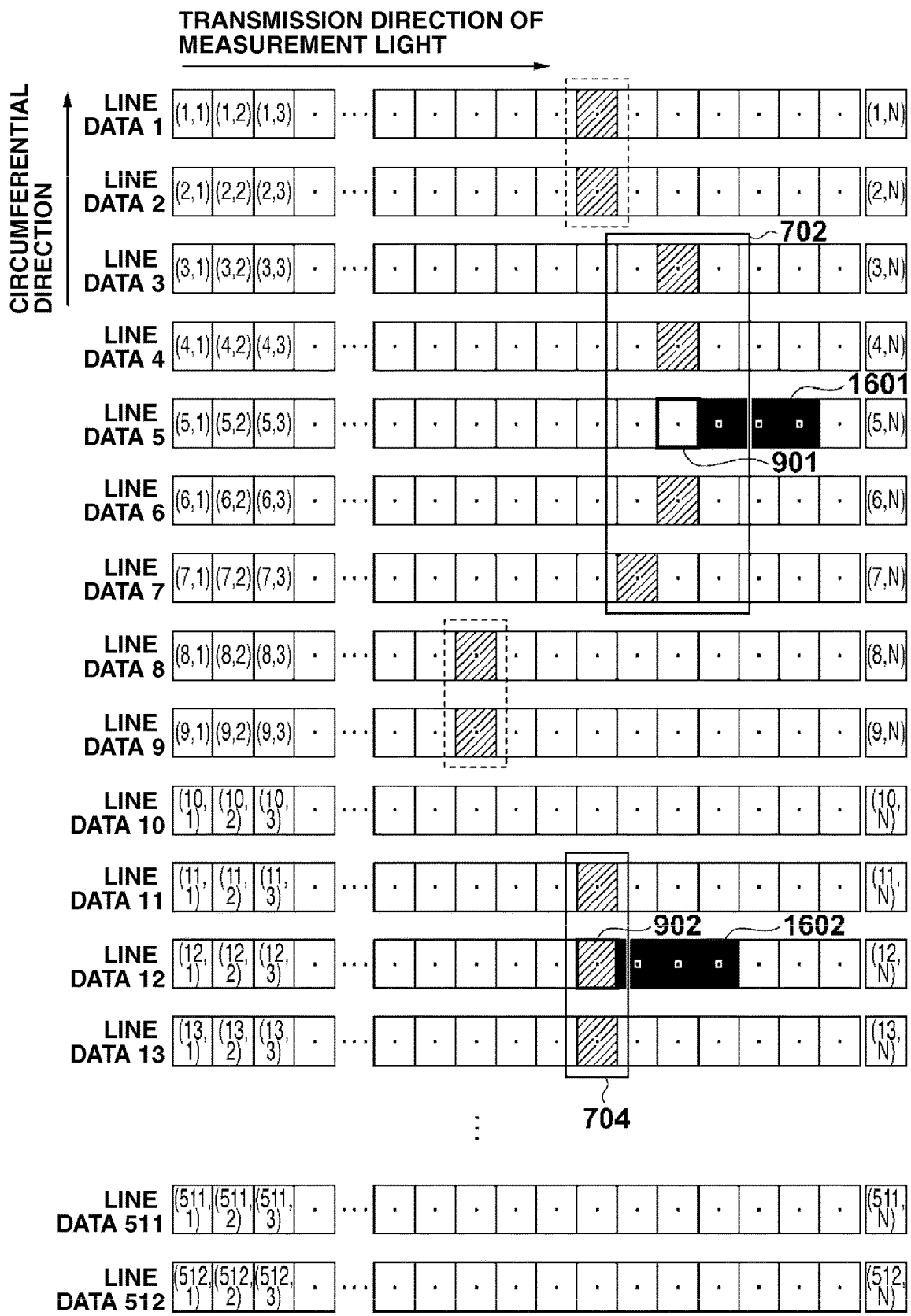
FIG. 16 is a diagram for explaining a general outline of an addition process of stent-thickness.

The already-described FIG. 9 shows an aspect in which representative points are extracted from the labeling groups 702 and 704 which were not eliminated in step S1506 and FIG. 16 shows an aspect in which indicators indicating the stent-thickness are added with respect to the aforesaid representative points. In the example of FIG. 9, the labeling group 702 is constituted by pixel data including five stent candidate-points (pixel data including stent candidate-points from lines 3 to 7 and pixel data having fluctuation for three pixels in the measurement light transmission direction). Consequently, a pixel 901 is extracted as the representative point from the labeling group 702. Similarly, a pixel 902 is extracted as the representative point from the labeling group 704 (see FIG. 9). Then, indicators 1601, 1602 are added with respect to the respective pixels 901, 902 (see FIG. 16).

Next, there will be explained a process for generating an inner-wall closed-curve by using inner-wall candidate-points. In step S1516, a labeling process is carried out with respect to pixel data of an inner-wall candidate-point in each of the detected line data.

Specifically, if the distance from the transmission and reception unit to the inner-wall candidate-point of the line data of the labeling processing target lies within a predetermined range with respect to the distance from the transmission and reception unit to the inner-wall candidate-point of the adjacent line data (line data on a line which is up by one line from the line of the labeling processing target), the same label as that of the inner-wall candidate-point on the adjacent line data is added thereto.

On the other hand, in a case in which the distance from the transmission and reception unit to the inner-wall candidate-point of the line data of the labeling processing target does not lie within the predetermined range with respect to the distance from the transmission and reception unit to the inner-wall candidate-point of the adjacent line data, a different label from that of the adjacent line data is added thereto.

The already-described FIG. 10 is a diagram showing an aspect in which the labeling process was carried out in step S1516 with respect to pixel data of an inner-wall candidate-point in each of the line data detected in step S1515.

In FIG. 10, cross-hatched pixel data express pixel data of inner-wall candidate-points. Also, dotted lines surrounding the peripheries of a plurality of inner-wall candidate-points show the fact that the same labels are added to the inner-wall candidate-points included in the aforesaid dotted lines. In an example of FIG. 10, there are shown one labeling group (labeling group 1001) which is composed of two inner-wall candidate-points and three labeling groups (labeling groups 1002 to 1004) each of which is composed of three inner-wall candidate-points.

In step S1517, fluctuation in the transmission direction of the measurement light for the inner-wall candidate-points (inner-wall candidate-points to which the same labels are added) which are included in each labeling group is found-out or determined; the aforesaid found-out fluctuation is compared with that of the adjacent labeling group each other; and the labeling group on the side in which the fluctuation is large is to be eliminated. This is because there is a high possibility, for the labeling group on the side in which the fluctuation in the transmission direction is large, noises are to be detected erroneously as inner-wall candidate-points.

The already-described FIG. 11 is a diagram showing an aspect in which the fluctuation in the transmission direction of the inner-wall candidate-points, for which the same labels are added with respect to the respective labeling groups shown in FIG. 10, is found-out; the aforesaid found-out fluctuation is compared with that of the adjacent labeling group each other; and the labeling group on the side in which the fluctuation is large was eliminated. In the example of FIG. 11, there is shown the fact that the labeling group 1002 and the labeling group 1004 are eliminated.

In step S1518, a representative point is extracted from each labeling group which was not eliminated in step S1517. Specifically, for the position of each inner-wall candidate-point included in each labeling group, a mid-value or average-value of the position of each inner-wall candidate-point in the transmission direction of the measurement light and a mid-value or average-value of the position of each inner-wall candidate-point in the circumferential direction are calculated respectively, and these are made to be data of the representative point (that is, the center position is found-out based on the positional information in the transmission direction and the circumferential direction of the inner-wall candidate-point and this is made to be the representative point).

The already-described FIG. 12 shows an aspect in which representative points are extracted from the labeling groups 1001 and 1003 which were not eliminated in step S1517. In the example of FIG. 12, the labeling group 1001 is constituted by pixel data including three inner-wall candidate-points (pixel data including inner-wall candidate-points from lines 1 and 2 and pixel data having fluctuation for one pixel in the measurement light transmission direction). Consequently, a pixel 1201 is extracted as the representative point from the labeling group 1001. Similarly, a pixel 1202 is extracted as the representative point from the labeling group 1003.

In step S1519, an inner-wall closed-curve is generated by using the representative points extracted in step S1518.

In step S1520, a tomographic image is reconstructed based on the line data added with the indicator indicating the stent-thickness and by superimposing the inner-wall closed-curve thereon, the indicator indicating the stent-thickness is added thereto and the tomographic image on which the inner-wall closed-curve is superimposed is displayed. The stent-thickness addition processing unit 1407 carrying out the step S1520 is an example of a reconstruction means for reconstructing, when the stent thickness is inputted, the tomographic image after changing the pixel data to include the number of pixels corresponding to the thickness of the stent into a display showing the stent toward the transmission direction from the detected stent position. The stent-thickness addition processing unit 1407 can be a computer (e.g computer installed software, or hardware for exclusive use) programmed or otherwise configured to carry out the step S1520.

3. Embodiment

Next, in accordance with a stent-thickness display process shown in FIG. 15, there will be explained an embodiment of a tomographic image in which indicators indicating the stent-thickness are added to the tomographic image and the inner-wall closed-curve is superimposed thereon.

Figure 17:
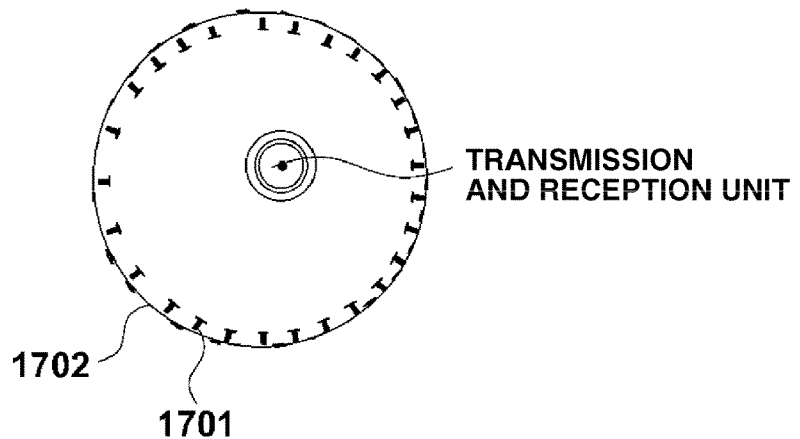
FIG. 17 is a diagram showing an embodiment of a display process of stent-thickness.

FIG. 17 is a diagram showing a tomographic image in which indicators indicating the stent-thickness are added and the inner-wall closed-curve is superimposed in accordance with the stent-thickness display process shown in FIG. 15.

In FIG. 17, a reference numeral 1701 expresses indicators indicating the stent-thickness and a reference numeral 1702 expresses the inner-wall closed-curve. As shown in FIG. 17, the indicators indicating the stent-thickness are extended as much as the stent-thickness radially from the transmission and reception unit by setting the representative points extracted in step S1508 to be the starting points. Thus, it becomes possible for the user, on the tomographic image, to confirm easily whether or not the outer surface of the stent contacts the inner-wall and in a case in which the outer surface of the stent is spaced apart from the inner-wall, to confirm rather easily how much the stent is spaced apart from the inner-wall.

As clear from the explanation above, in the optical imaging apparatus for diagnosis relating to this embodiment, there is employed a constitution or configuration in which information relating to the stent-thickness is displayed as the indicator on the tomographic image and concurrently, the inner-wall closed-curve is displayed thereon.

As a result, in the optical imaging apparatus for diagnosis, it is possible to confirm the thickness of the indwelled stent easily on the tomographic image.

Third Embodiment

In the above-described second embodiment, there was employed, on an occasion of displaying information relating to the stent-thickness, a constitution or configuration in which the indicators are arranged in the radial direction from the representative points of the labeling group, which are composed of the stent candidate-points, but the invention is not limited by this aspect.

For example, it is possible to employ a constitution or configuration in which there is generated a stent closed-curve based on the representative points of the labeling groups, which are composed of stent candidate-points; in which there is generated a closed curve which is a closed curve analogous with respect to the stent closed-curve and which is arranged by maintaining a distance equivalent to the stent-thickness with respect to the stent closed-curve; and in which they are to be displayed.

Figure 18:
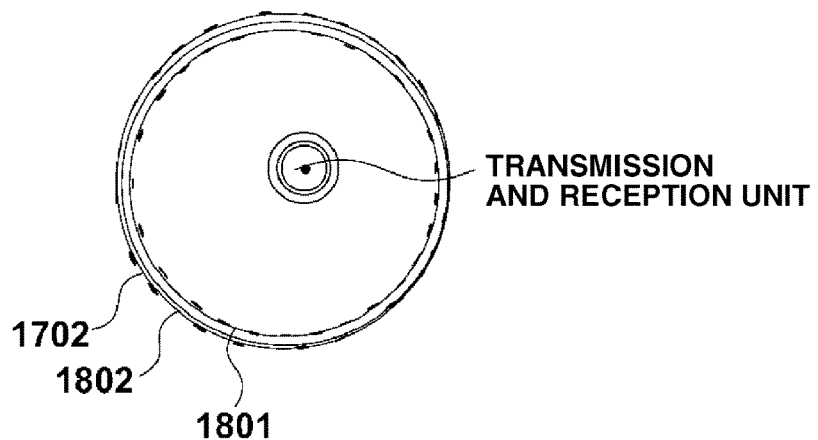
FIG. 18 is a diagram showing another embodiment of a display process of stent-thickness.

FIG. 18 is a diagram showing one example of a case in which the stent-thickness is displayed by a stent closed-curve and a closed curve analogous to the above-described closed-curve.

In FIG. 18, a reference numeral 1801 indicates a stent closed-curve generated based on the representative points extracted in step S1508. Also, a reference numeral 1802 indicates a closed curve which is separated by a distance (clearance between 1801 and 1802) corresponding to the stent-thickness with respect to the stent closed-curve 1801 and which is analogous with respect to the stent closed-curve 1801. The reference numeral 1702 indicates an inner-wall closed-curve.

In this manner, by generating the closed curves 1801, 1802 and by displaying them by being superimposed with the tomographic image, it becomes possible for a user to comprehend the stent-thickness visually on the tomographic image. Also, by displaying the closed curve 1702 of the inner-wall together, it becomes possible, on the tomographic image, to confirm rather easily whether or not the outer surface of the stent contacts the inner-wall and in a case in which the outer surface of the stent is spaced apart from the inner-wall, to confirm rather easily how much the stent outer surface is spaced apart from the inner-wall.

Fourth Embodiment

The above-described third embodiment employs a constitution or configuration in which the stent-thickness is expressed by two lines of closed curves 1801, 1802, but the invention is not limited in this regard. For example, it is possible to employ a constitution or configuration in which the stent-thickness is expressed by painting and filling the region surrounded (located between) by the two lines of the closed curves 1801, 1802 depending on a predetermined display format (for example, by a predetermined color).

Figure 19:
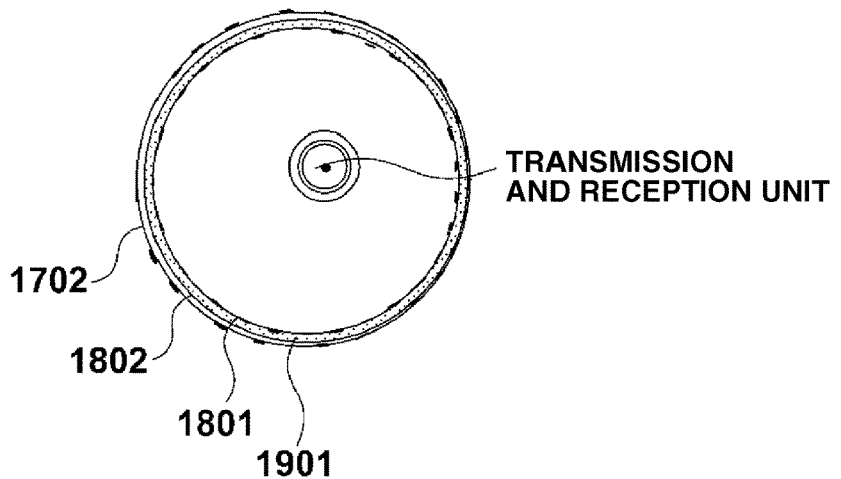
FIG. 19 is a diagram showing another embodiment of a display process of stent-thickness.

FIG. 19 is a diagram showing one example in which the stent-thickness is displayed by painting and filling the region surrounded by the stent closed-curve and a closed curve analogous with the aforesaid closed curve by using a pre-determined color.

In FIG. 19, a reference numeral 1801 indicates a stent closed-curve which was generated based on the representative points extracted in step S1508. Also, a reference numeral 1802 indicates a closed curve which is analogous to the stent closed-curve 1801 and which is arranged with respect to the stent closed-curve 1801 by being separated with a distance as many as the stent-thickness. Further, a reference numeral 1901 indicates a region surrounded by the closed curve 1801 and the closed curve 1802, in which it shows that the stent exists in the aforesaid region. Reference numeral 1702 indicates an inner-wall closed-curve.

In this manner, by generating the closed curves 1801, 1802; by painting and filling the region surrounded by the aforesaid closed curves with a predetermined color; and by displaying the region on the tomographic image, it becomes possible for a user to visually-comprehend the stent-thickness easily on the tomographic image. Also, by displaying the inner-wall closed-curve together, it becomes possible, on the tomographic image, to confirm easily whether or not the outer surface of the stent contacts with the inner-wall and in a case in which the outer surface of the stent is apart from the inner-wall, to confirm easily how much degree it is apart therefrom.

The detailed description above describes embodiments of an optical imaging apparatus for diagnosis and an image processing method representing examples of the optical imaging apparatus and image processing method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An optical imaging apparatus for diagnosis which obtains reflection light from biological tissue of a body lumen by moving a transmission and reception unit, that carries out optical transmission and reception, continuously in an axial direction while rotating the unit in a circumferential direction inside the body lumen, and which constructs a tomographic image of the biological tissue using line data of interference light obtained by making the obtained reflection light and a reference light interfere with each other, the optical imaging apparatus comprising:
   first analysis means for reading-out line data used for constructing a predetermined tomographic image and for analyzing intensity change in transmission direction of the light from the transmission and reception unit for every line data;
   first detection means for detecting, based on the analysis result by the first analysis means, pixel data expressing a stent position for every line data;
   input means for inputting information identifying a thickness of the stent; and
   reconstruction means for reconstructing, when the stent thickness is inputted to the input means, the tomographic image by changing the pixel data for each of a plurality of the line data to include an additional number of pixels in the transmission direction so that the number of pixels in the pixel data for each of the plurality of the line data corresponds to the thickness of the stent in a display showing the stent,
   wherein the first analysis means analyzes the intensity change by finding average inclination of the line data within a predetermined range in the transmission direction for every predetermined distance, and the first detection means detects pixel data in which the intensity change becomes maximum.

2. The optical imaging apparatus for diagnosis according to claim 1, wherein the reconstruction means further comprises:
   labeling means for labeling each pixel data expressing the stent position detected for every line data based on positional information of each pixel data;
   elimination means for eliminating, within respective labeling groups applied with the same labels in the labeling means, labeling groups in which the number of pixel data in circumferential direction, which is included in one labeling group, is a predetermined value or less;
   calculation means for calculating a center position of each labeling group, which was not eliminated in the elimination means, based on the positional information of each pixel data, and wherein
   the tomographic image is reconstructed, after changing the pixel data for the number of pixels corresponding to the thickness of the stent, into a display showing the stent toward the transmission direction from the center position calculated by the calculation means.

3. The optical imaging apparatus for diagnosis according to claim 1, further comprising:
   second analysis means for reading-out line data used for a construction of a predetermined tomographic image and for analyzing maximum intensity in the transmission direction of light from the transmission and reception unit for every line data;
   second detection means for detecting pixel data expressing inner-wall position for every line data based on the analysis result by the second analysis means;
   labeling means for labeling each pixel data expressing the inner-wall position detected for every line data based on positional information of each pixel data;
   elimination means for eliminating a labeling group in which the variation of positional information of pixel data, included in one labeling group within the respective labeling groups applied with the same labels by the labeling means, in the transmission direction is larger than a predetermined variation;
   calculation means for calculating, with regard to each labeling group which was not eliminated by the elimination means, center position of the labeling group based on positional information of each pixel data of the labeling group; and
   generation means for generating an inner-wall closed-curve by using the center position of each labeling group, which was calculated by the calculation means.

4. An image processing method of an optical imaging apparatus for diagnosis which obtains reflection light from biological tissue of a body lumen by moving a transmission and reception unit, that carries out optical transmission and reception, continuously in an axial direction while rotating the unit in a circumferential direction inside the body lumen, and which constructs a tomographic image of the biological tissue using line data of interference light obtained by making the obtained reflection light and a reference light interfere with each other, the method comprising:
   reading-out line data used for construction of a predetermined tomographic image and for analyzing intensity change in transmission direction of the light from the transmission and reception unit for every line data;

detecting, based on a result of the analyzing of the intensity change, pixel data expressing stent position for every line data;

inputting information relating to thickness of the stent; and reconstructing the tomographic image, when an instruction is inputted that the thickness of the stent is to be displayed, by changing the pixel data for each of a plurality of the line data to include an additional number of pixels in the transmission direction so that the number of pixels in the pixel data for each of the plurality of the line data corresponds to the thickness of the stent in a display showing the stent, wherein the intensity change is analyzed by finding average inclination of the line data within a predetermined range in the transmission direction for every predetermined distance, and the pixel data in which the intensity change becomes maximum is detected.

5. The image processing method of an optical imaging apparatus for diagnosis according to claim 4, wherein the reconstruction process further comprises:

labeling process for labeling each pixel data expressing the stent position detected for every line data based on positional information of each pixel data;

elimination process for eliminating, within the respective labeling groups applied with the same labels in the labeling process, labeling groups in which the number of pixel data in circumferential direction, which is included in one labeling group, is a predetermined value or less;

calculation process for calculating a center position of each labeling group, which was not eliminated in the elimination process, based on positional information of each pixel data; and wherein the tomographic image is reconstructed after changing the pixel data for the number of pixels corresponding to the thickness into a display showing the stent toward the transmission direction from the center position calculated in the calculation process.

* * * * *